US010048172B2

(12) United States Patent
Sugaya et al.

(10) Patent No.: US 10,048,172 B2
(45) Date of Patent: Aug. 14, 2018

(54) SUBSTANCE-TESTING APPARATUS, SUBSTANCE-TESTING SYSTEM, AND SUBSTANCE-TESTING METHOD

(71) Applicant: Hitachi, Ltd., Chiyoda-ku, Tokyo (JP)

(72) Inventors: Masakazu Sugaya, Tokyo (JP); Hideo Kashima, Tokyo (JP); Koichi Terada, Tokyo (JP); Yasuaki Takada, Tokyo (JP); Hisashi Nagano, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 58 days.

(21) Appl. No.: 15/128,358

(22) PCT Filed: Mar. 24, 2014

(86) PCT No.: PCT/JP2014/058096
§ 371 (c)(1),
(2) Date: Sep. 22, 2016

(87) PCT Pub. No.: WO2015/145546
PCT Pub. Date: Oct. 1, 2015

(65) Prior Publication Data
US 2017/0102296 A1 Apr. 13, 2017

(51) Int. Cl.
*G01N 1/22* (2006.01)
*G01N 1/40* (2006.01)
*G01N 1/02* (2006.01)

(52) U.S. Cl.
CPC ......... *G01N 1/2202* (2013.01); *G01N 1/4022* (2013.01); *G01N 2001/022* (2013.01);
(Continued)

(58) Field of Classification Search
CPC ............... G01N 1/2202; G01N 1/4022; G01N 2001/024; G01N 2001/2223; G01N 2001/022; G01N 2001/4033
(Continued)

(56) References Cited

U.S. PATENT DOCUMENTS 4,909,089 A  3/1990 Achter et al.
5,109,691 A  5/1992 Corrigan et al.
(Continued)

FOREIGN PATENT DOCUMENTS

EP    1365226 A2 * 11/2003 ............... G01N 1/22
JP    54-156591 U    10/1979
(Continued)

OTHER PUBLICATIONS

Japanese Office Action issued in counterpart Japanese Application No. 2016-509646 dated Feb. 28, 2017 with unverified English translation (six pages).
(Continued)

Primary Examiner — Jonathan Dunlap
(74) Attorney, Agent, or Firm — Crowell & Moring LLP

(57) ABSTRACT

In order to save a space for an apparatus for inspecting a substance and reduce a cost thereof, a particle testing apparatus includes a plurality of collection ports for collecting substances to be inspected, centrifuges for concentrating particles collected in the collection ports, the centrifuges being connected to the respective collection ports in pairs, and a common analysis apparatus for acquiring the concentrated particles from the centrifuges and analyzing the particles, the analysis apparatus being connected to the centrifuges.

14 Claims, 23 Drawing Sheets

(52) U.S. Cl.
CPC ............... *G01N 2001/024* (2013.01); *G01N 2001/2223* (2013.01); *G01N 2001/4033* (2013.01)

(58) Field of Classification Search
USPC .......... 73/23.2, 23.31, 31.01, 31.02, 863.11, 73/863.31–863.33
See application file for complete search history.

(56) References Cited

U.S. PATENT DOCUMENTS

| | | | |
|---|---|---|---|
| 5,753,832 A | 5/1998 | Bromberg et al. | |
| 5,760,314 A | 6/1998 | Bromberg et al. | |
| 6,151,952 A | 11/2000 | Mathews et al. | |
| 6,326,623 B1 | 12/2001 | Chiba et al. | |
| 7,091,870 B2* | 8/2006 | Tsutsumi | H01J 49/04 250/288 |
| 7,516,351 B2* | 4/2009 | Inami | G06F 11/2294 702/20 |
| 8,284,051 B2* | 10/2012 | Takada | G08B 31/00 340/540 |
| 9,214,324 B2* | 12/2015 | Nagano | G01N 1/2214 |
| 9,417,163 B2* | 8/2016 | Nagano | G01N 1/2211 |
| 9,850,696 B2* | 12/2017 | Sugaya | E05F 15/40 |
| 2009/0014638 A1* | 1/2009 | Itou | G01V 5/0008 250/281 |
| 2009/0184820 A1* | 7/2009 | Takada | G08B 21/12 340/540 |
| 2012/0139736 A1* | 6/2012 | Suzuki | G01T 1/178 340/632 |
| 2014/0151543 A1 | 6/2014 | Nagano et al. | |
| 2014/0183256 A1* | 7/2014 | Calio | G01N 1/2208 235/375 |
| 2014/0238106 A1 | 8/2014 | Kashima et al. | |
| 2014/0260542 A1* | 9/2014 | Nagano | G01N 1/2211 73/28.04 |
| 2015/0136975 A1 | 5/2015 | Sugaya et al. | |
| 2015/0235831 A1* | 8/2015 | Nagano | G01N 1/2211 73/863.11 |

FOREIGN PATENT DOCUMENTS

| | | |
|---|---|---|
| JP | 2-198333 A | 8/1990 |
| JP | 9-126966 A | 5/1997 |
| JP | 2000-2767 A | 1/2000 |
| WO | WO 2012/063796 A1 | 5/2012 |
| WO | WO 2013/051530 A1 | 4/2013 |
| WO | WO 2013/175947 A1 | 11/2013 |

OTHER PUBLICATIONS

International Search Report (PCT/ISA/210) issued in PCT Application No. PCT/JP2014/058096 dated Jun. 24, 2014, with English translation (four (4) pages).

* cited by examiner

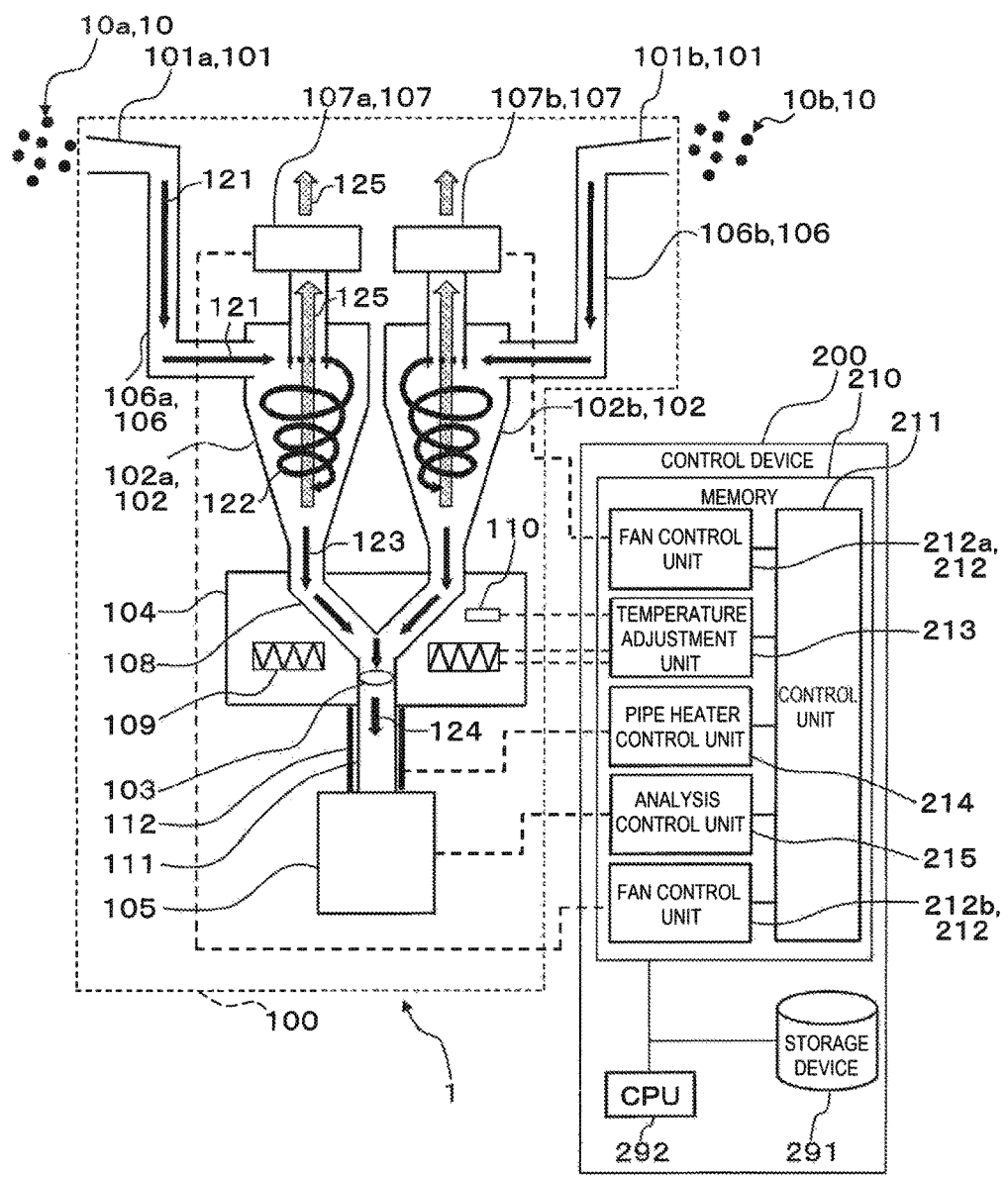
[FIG. 1]

[FIG. 2]
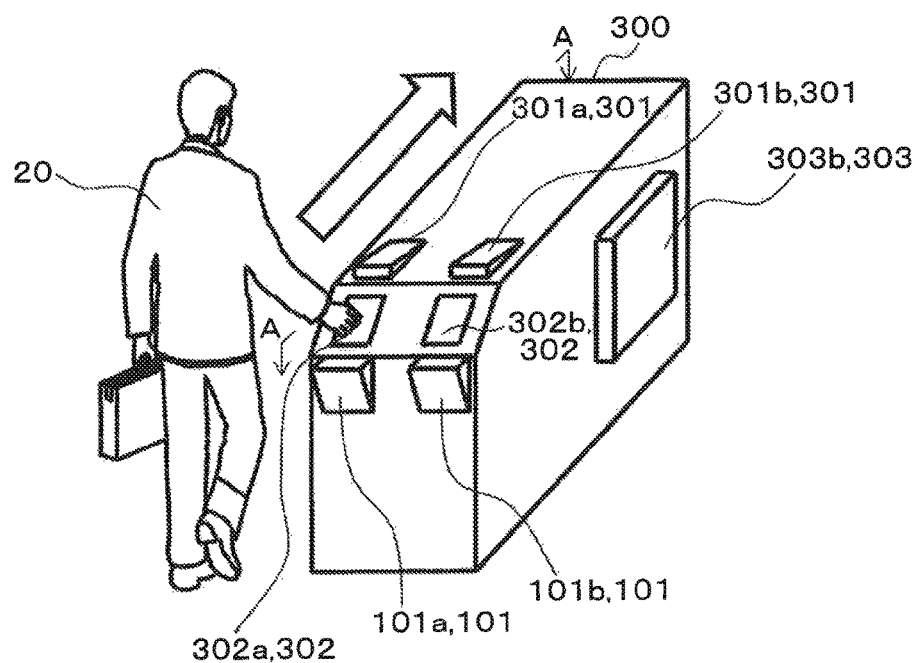
[FIG. 3]
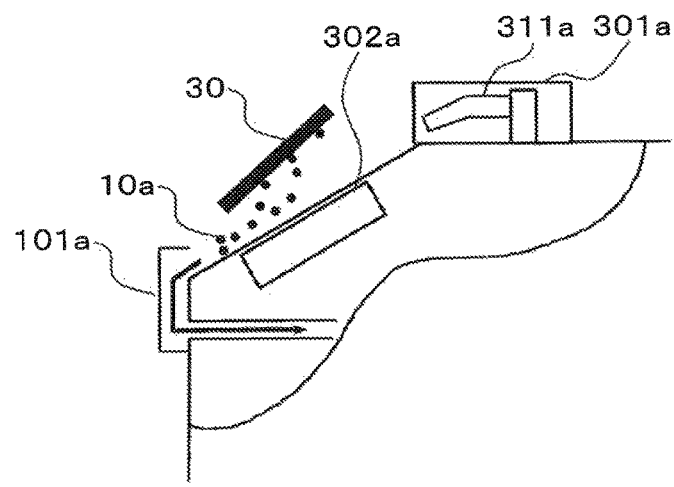

[FIG. 4]
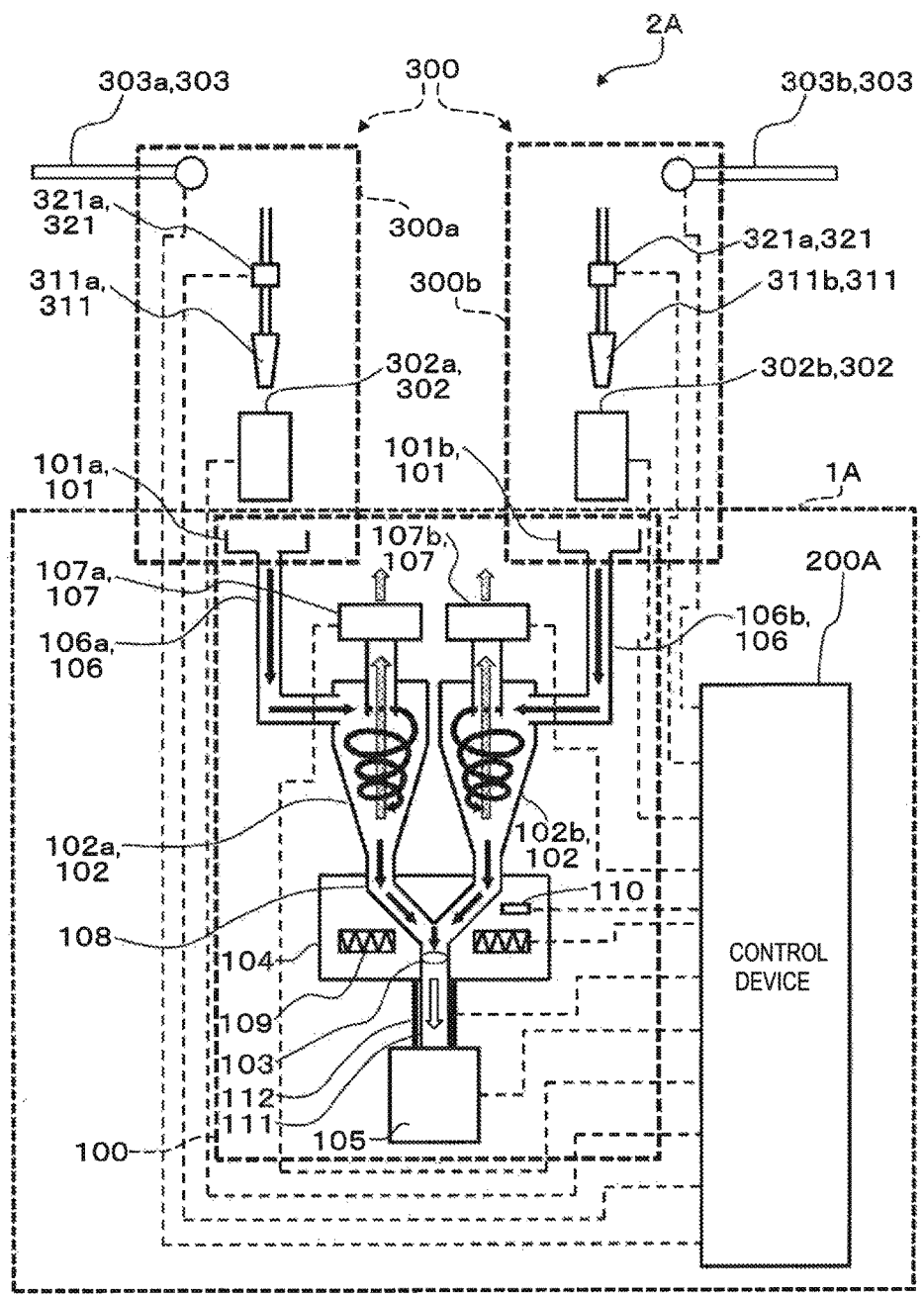

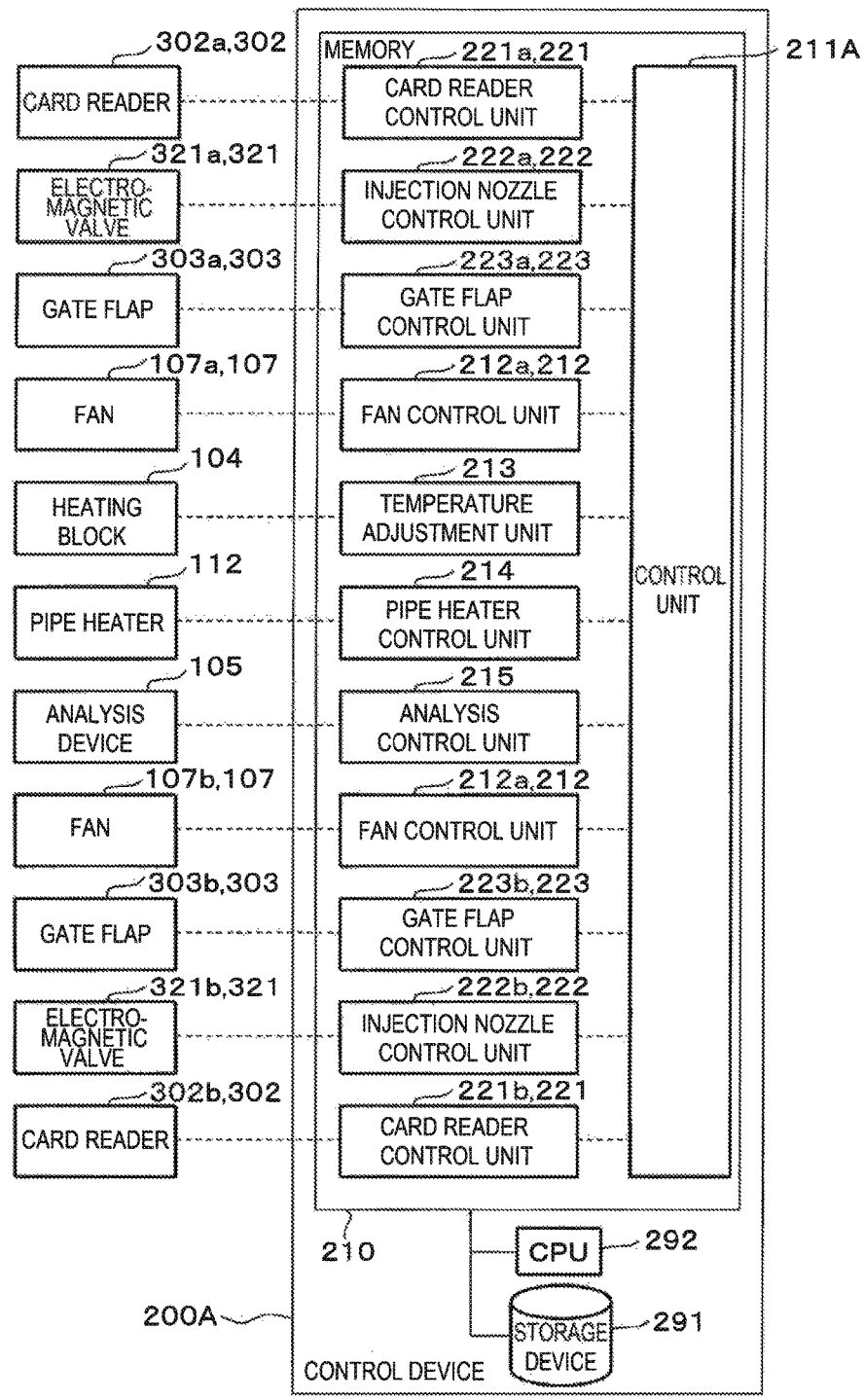

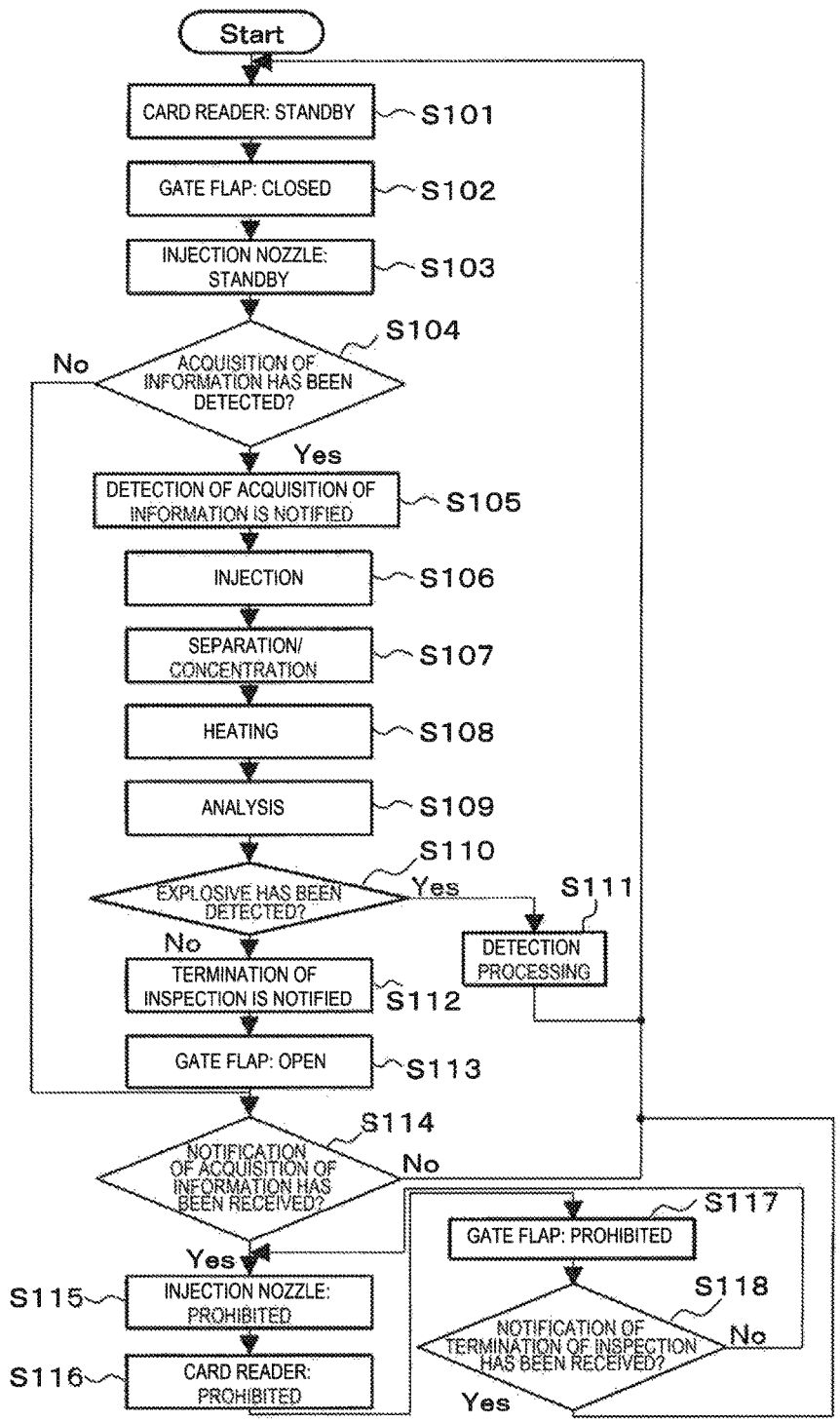
[FIG. 6]

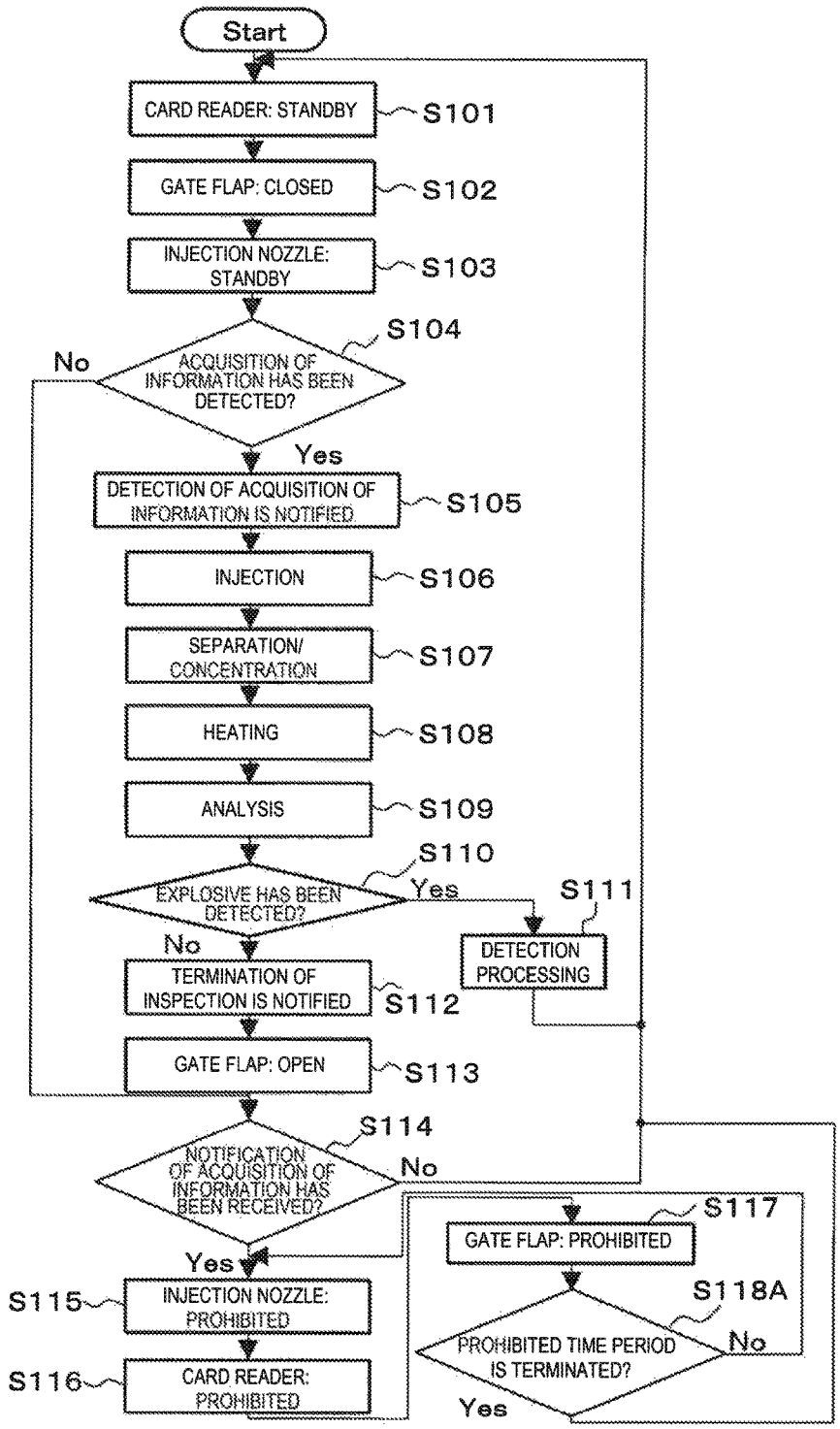
[FIG. 7]

[FIG. 10]
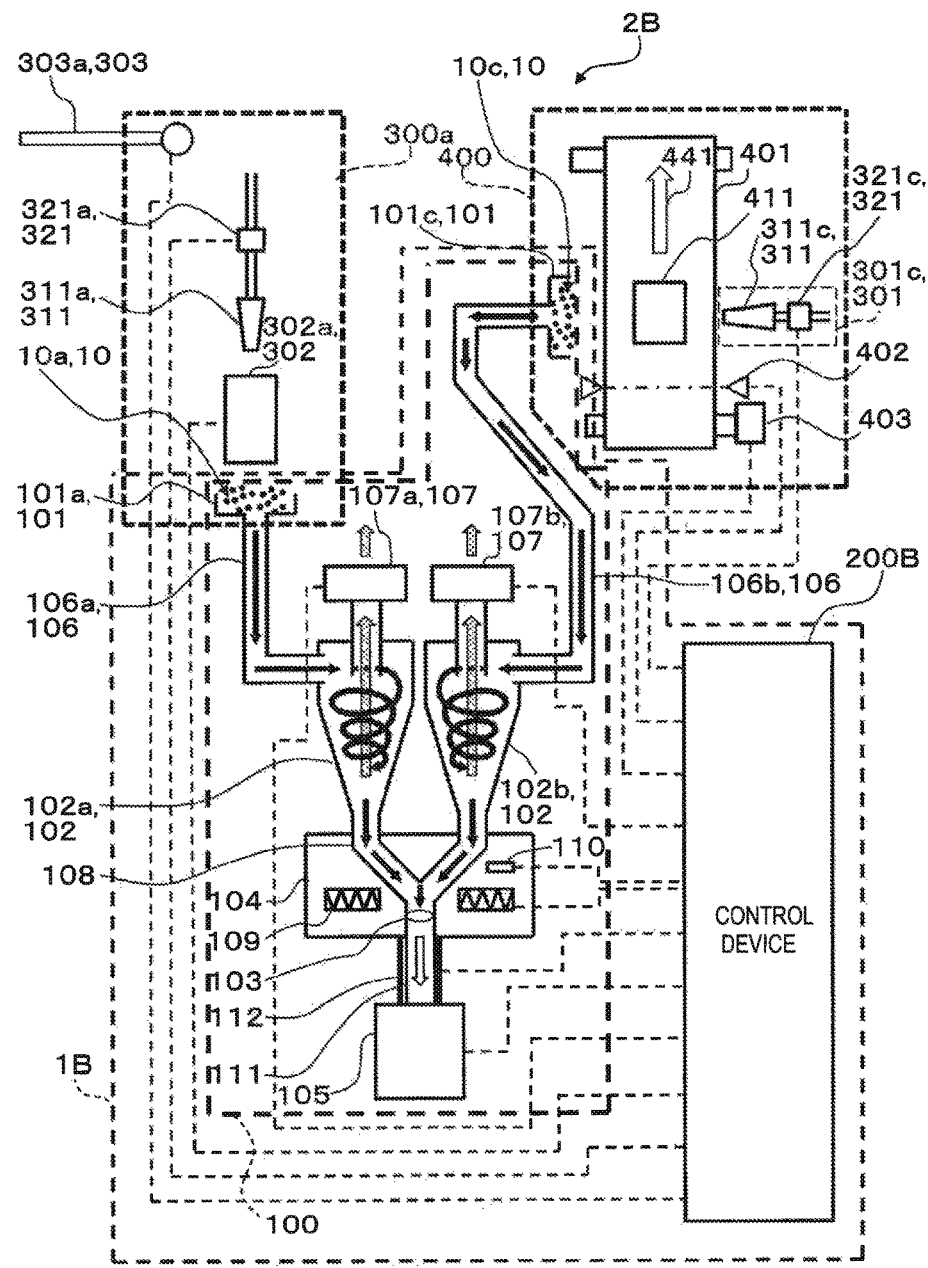

[FIG. 11]
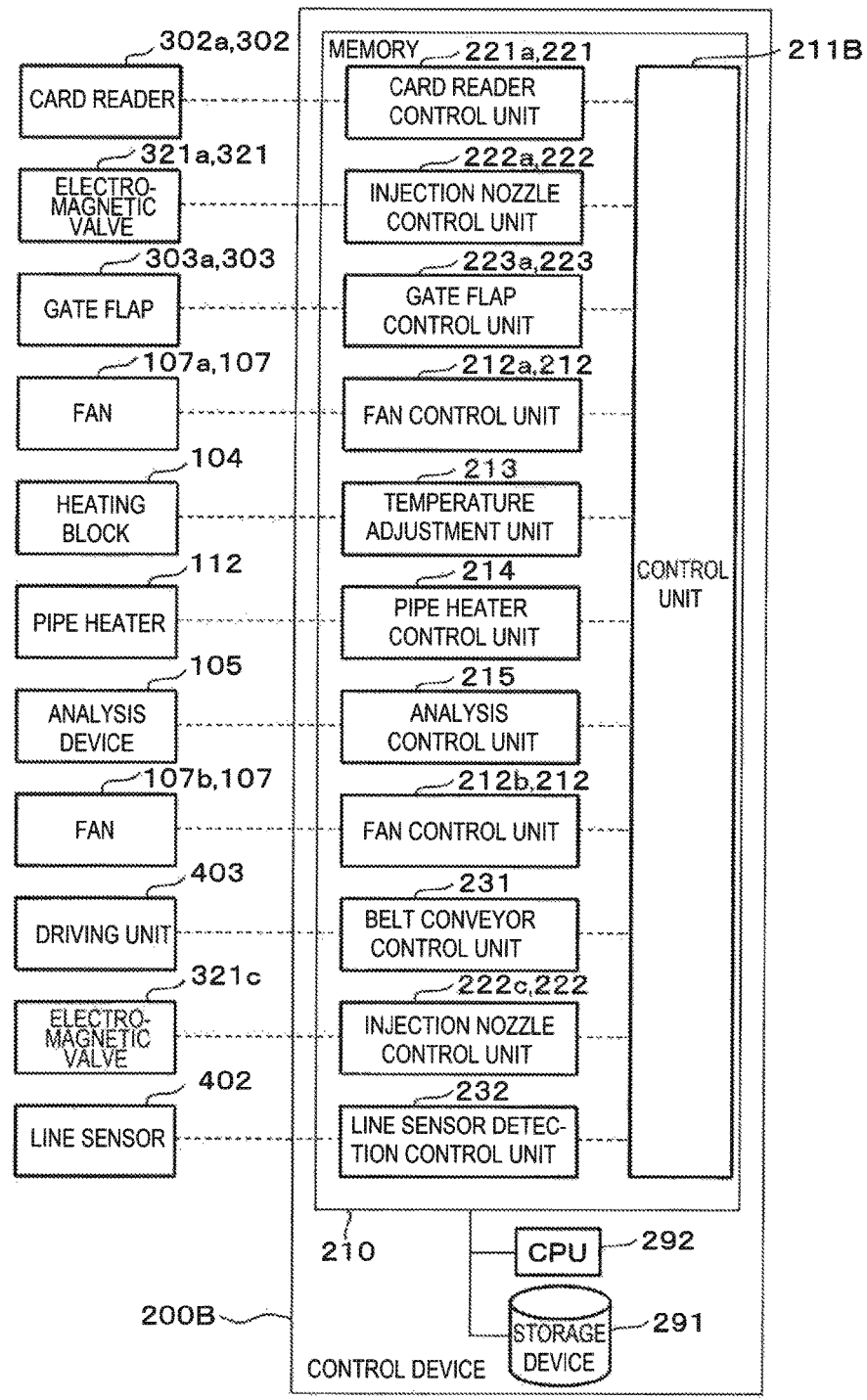

[FIG. 12]
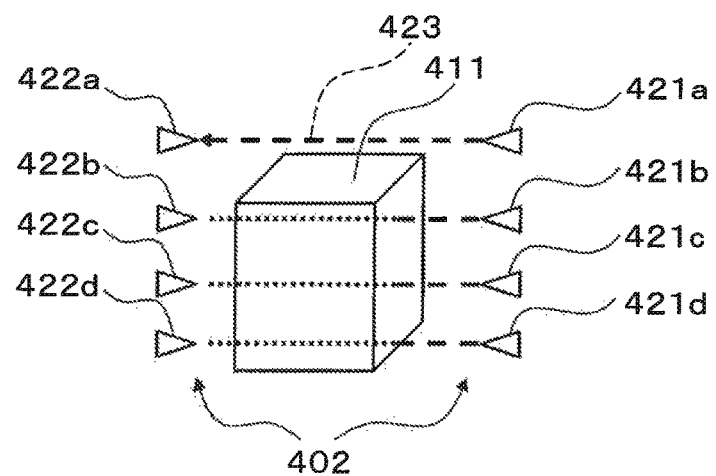
[FIG. 13]
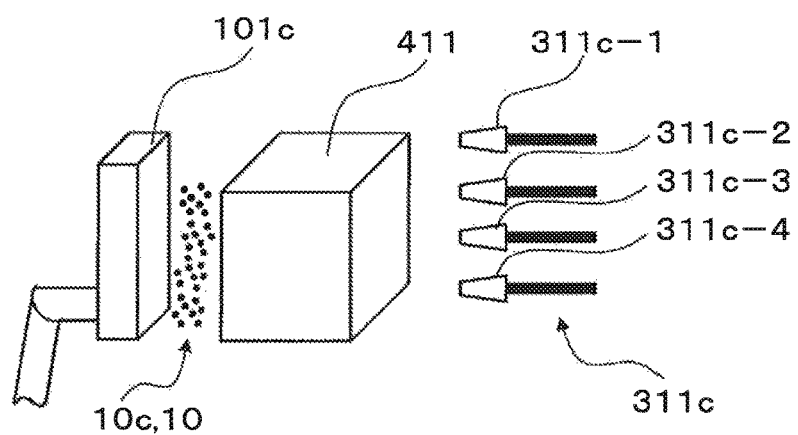

[FIG. 14]
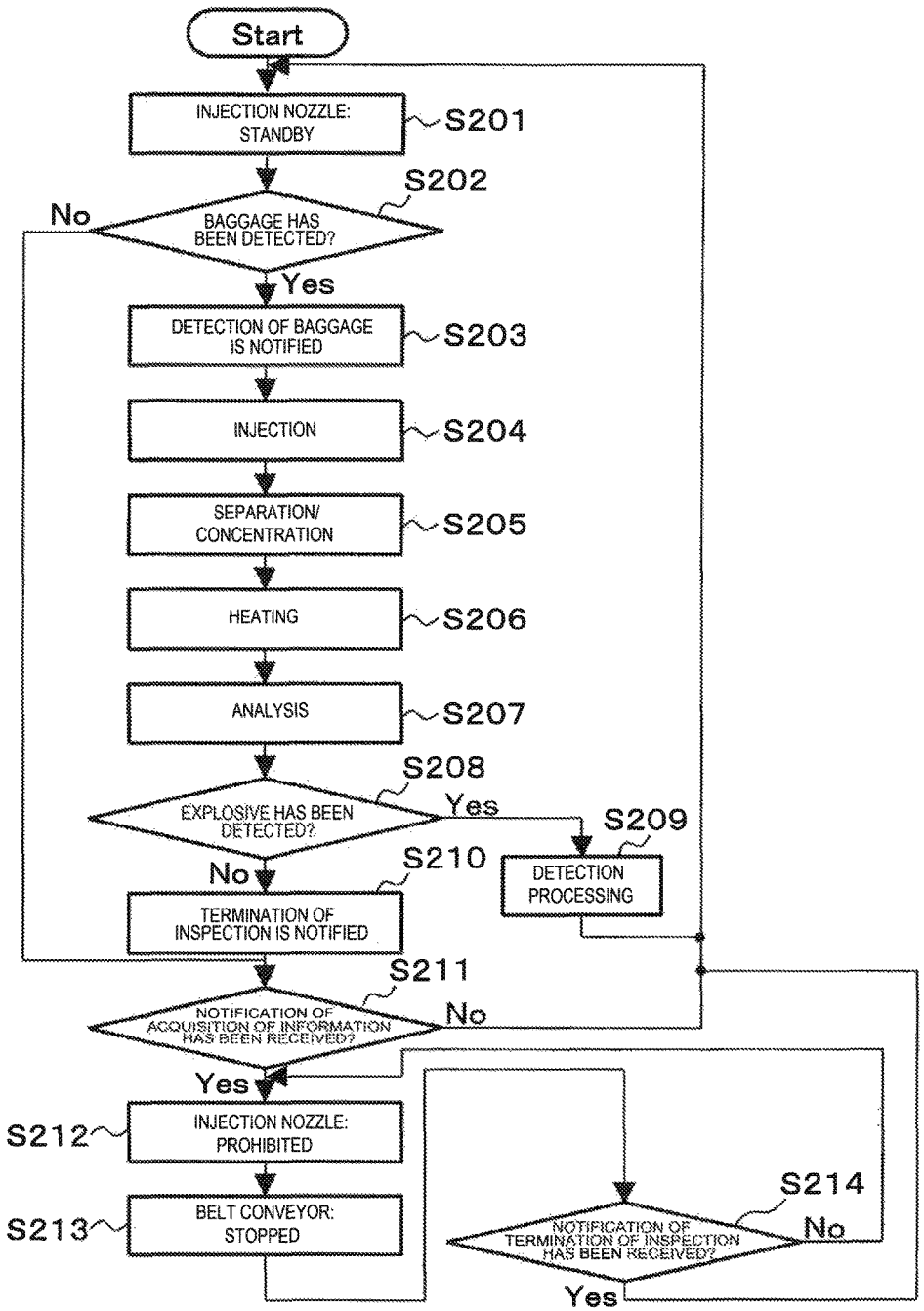

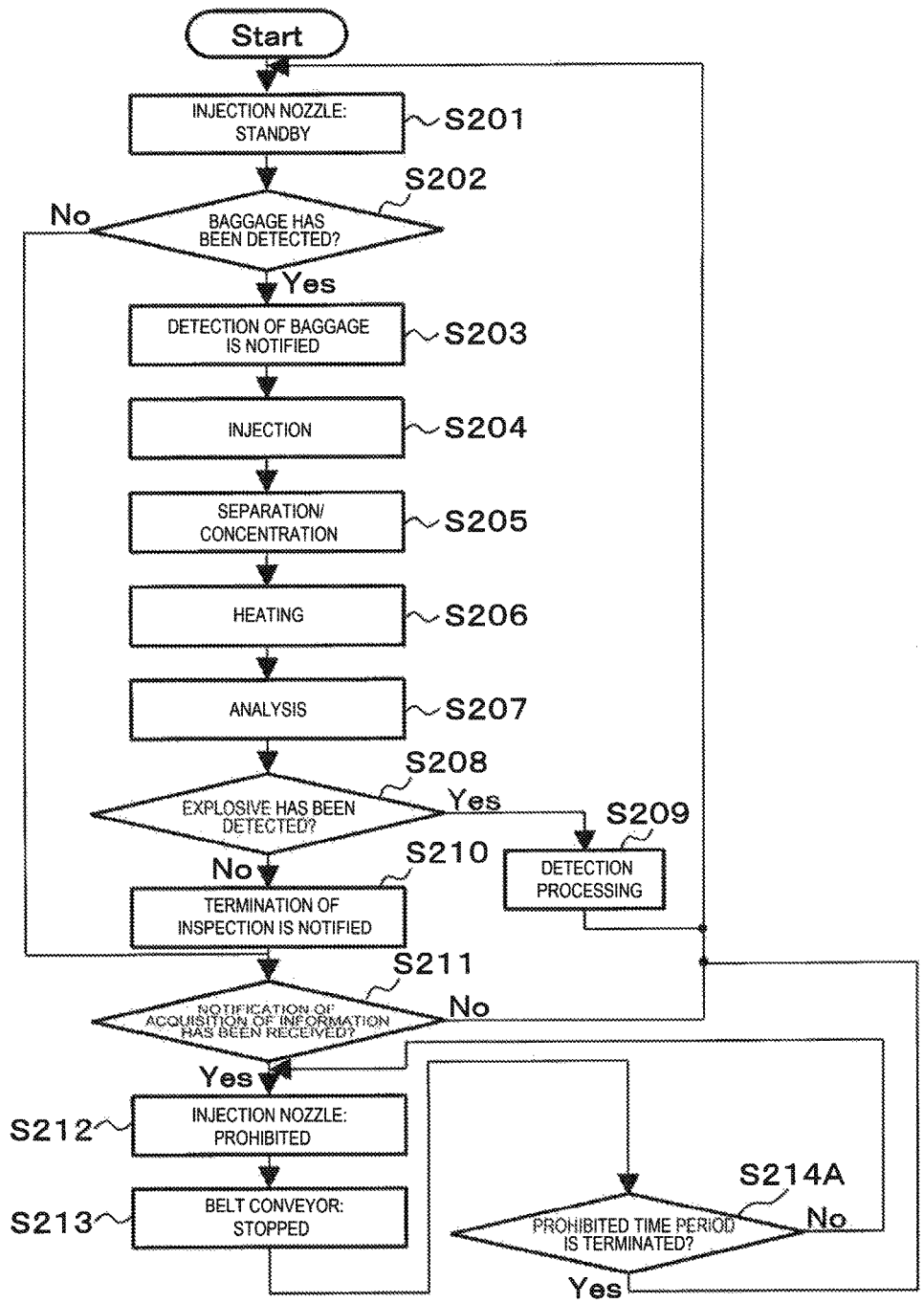
[FIG. 15]

[FIG. 16]
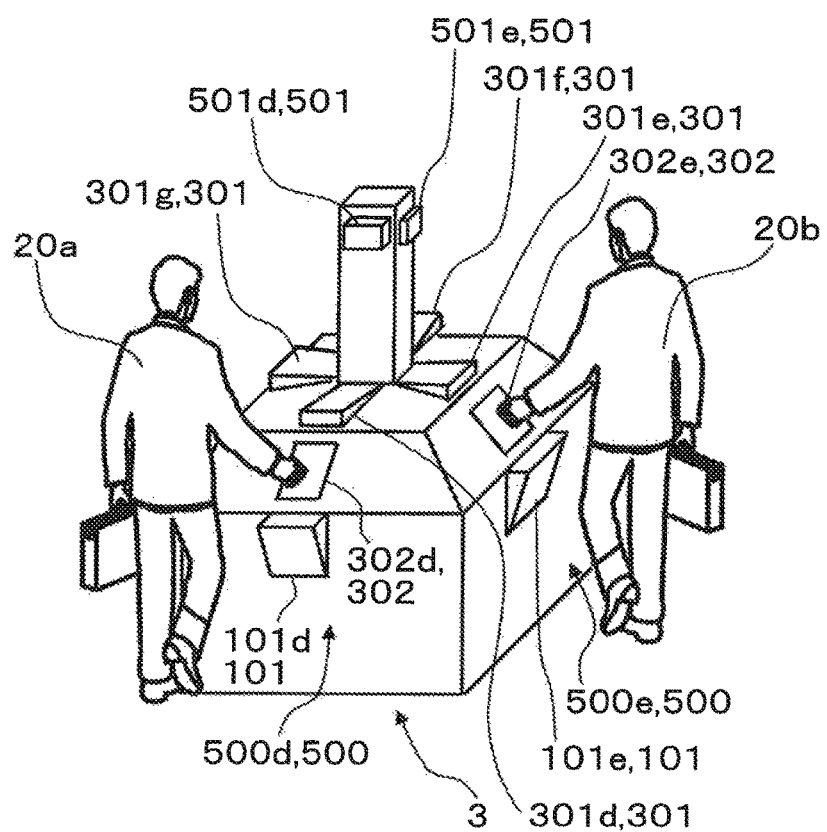

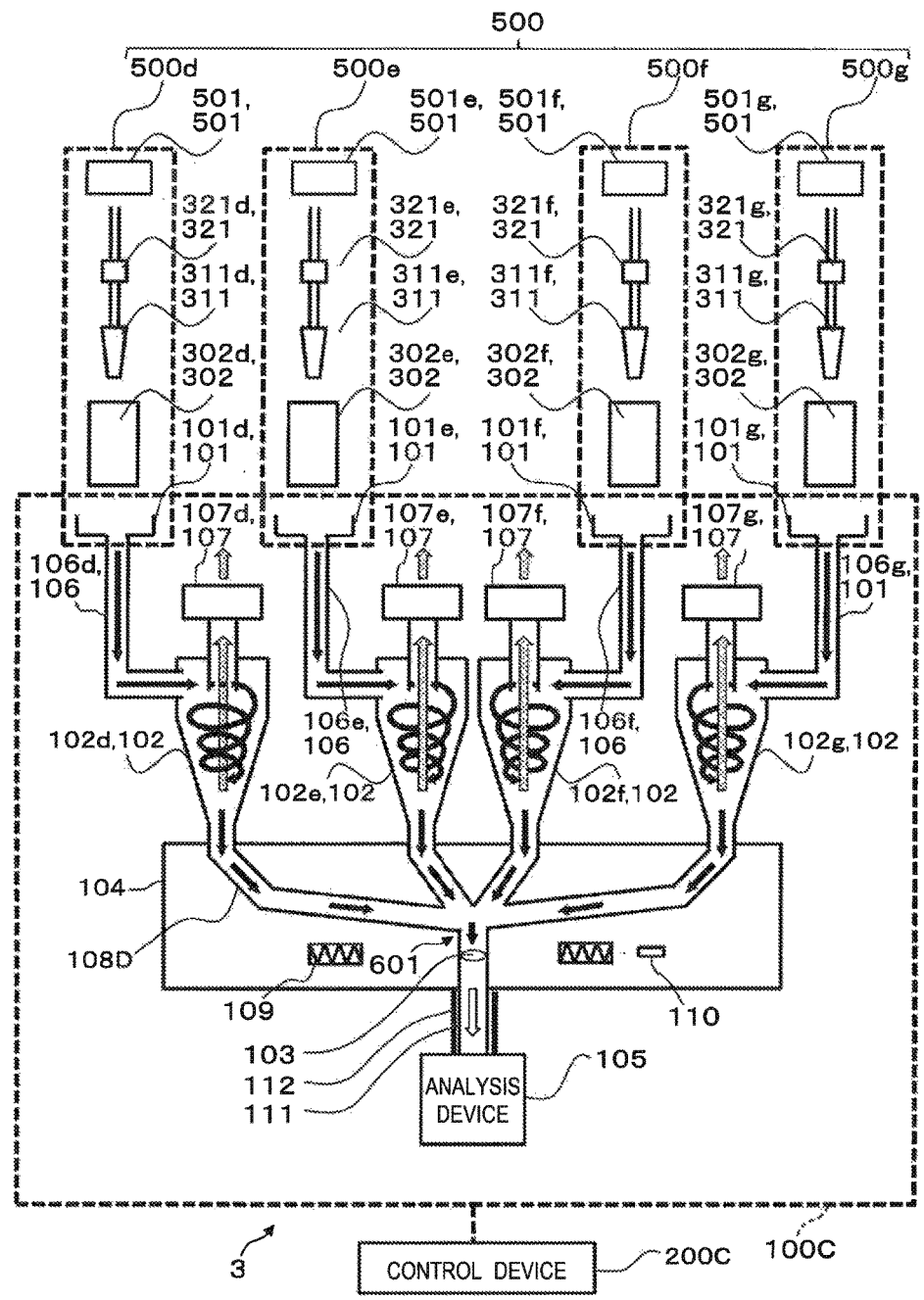
[FIG. 17]

[FIG. 18]
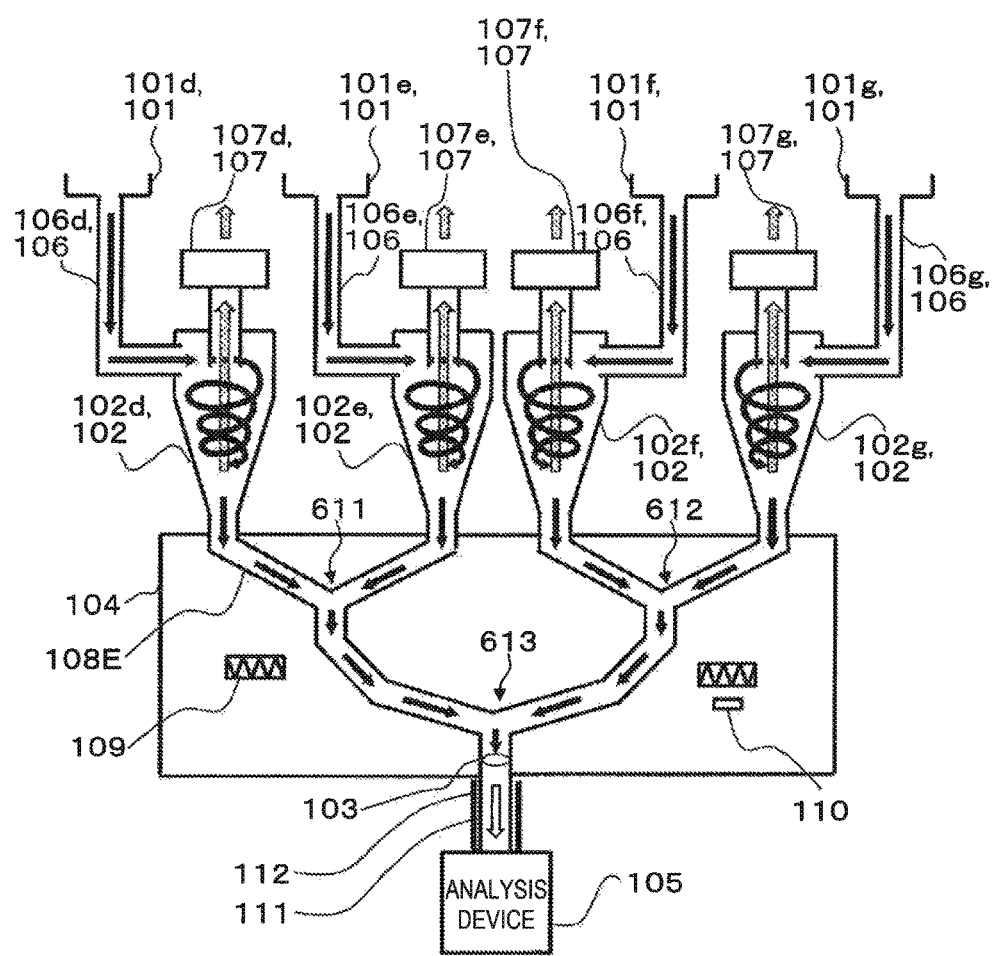

[FIG. 19]
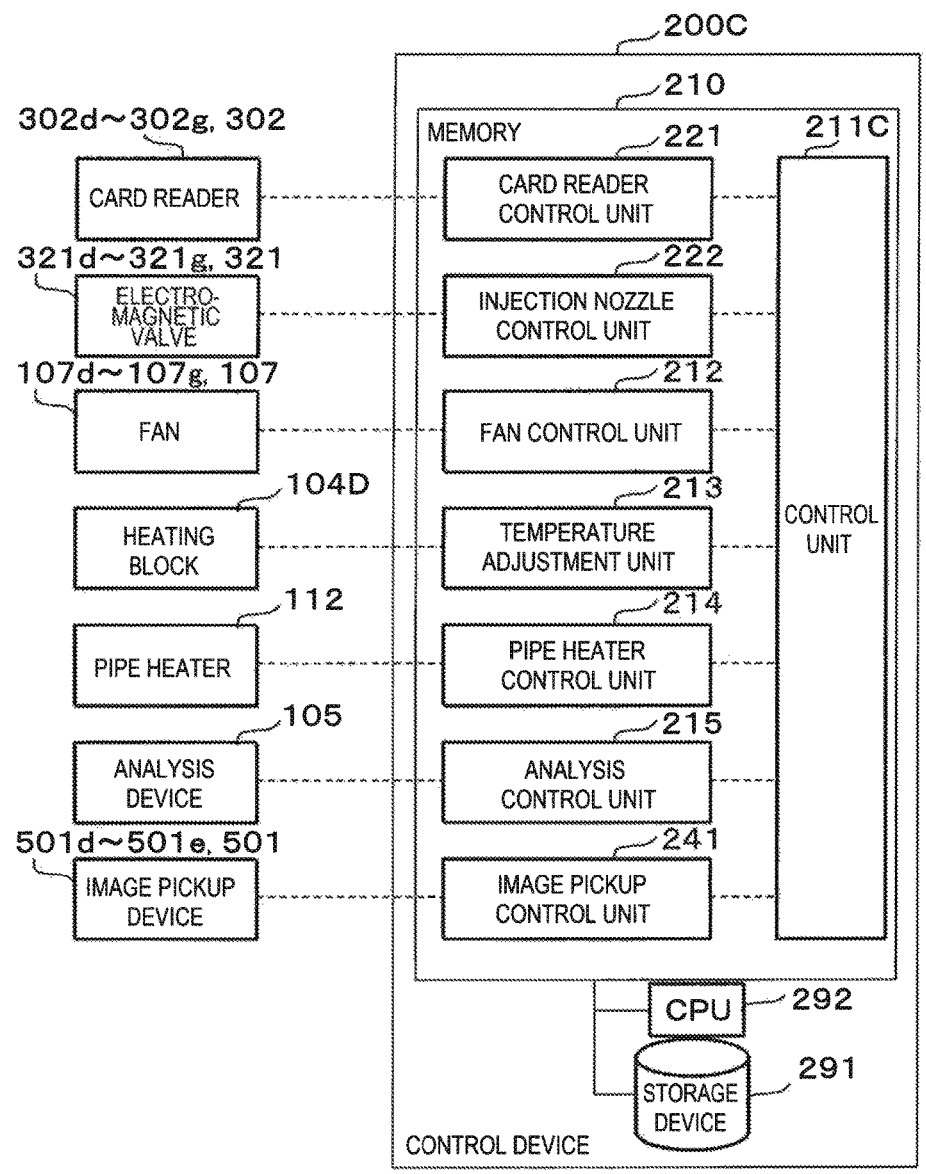

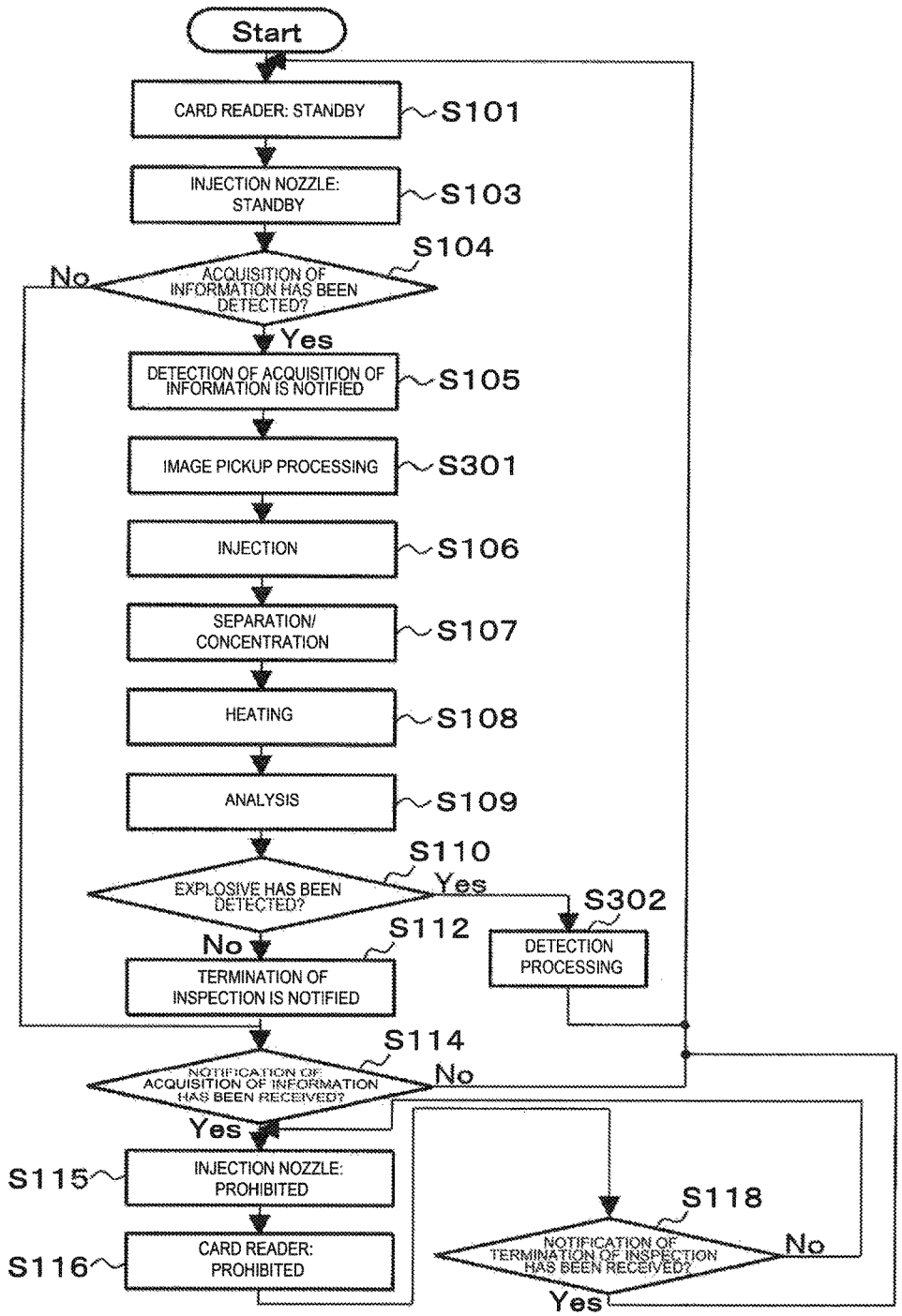

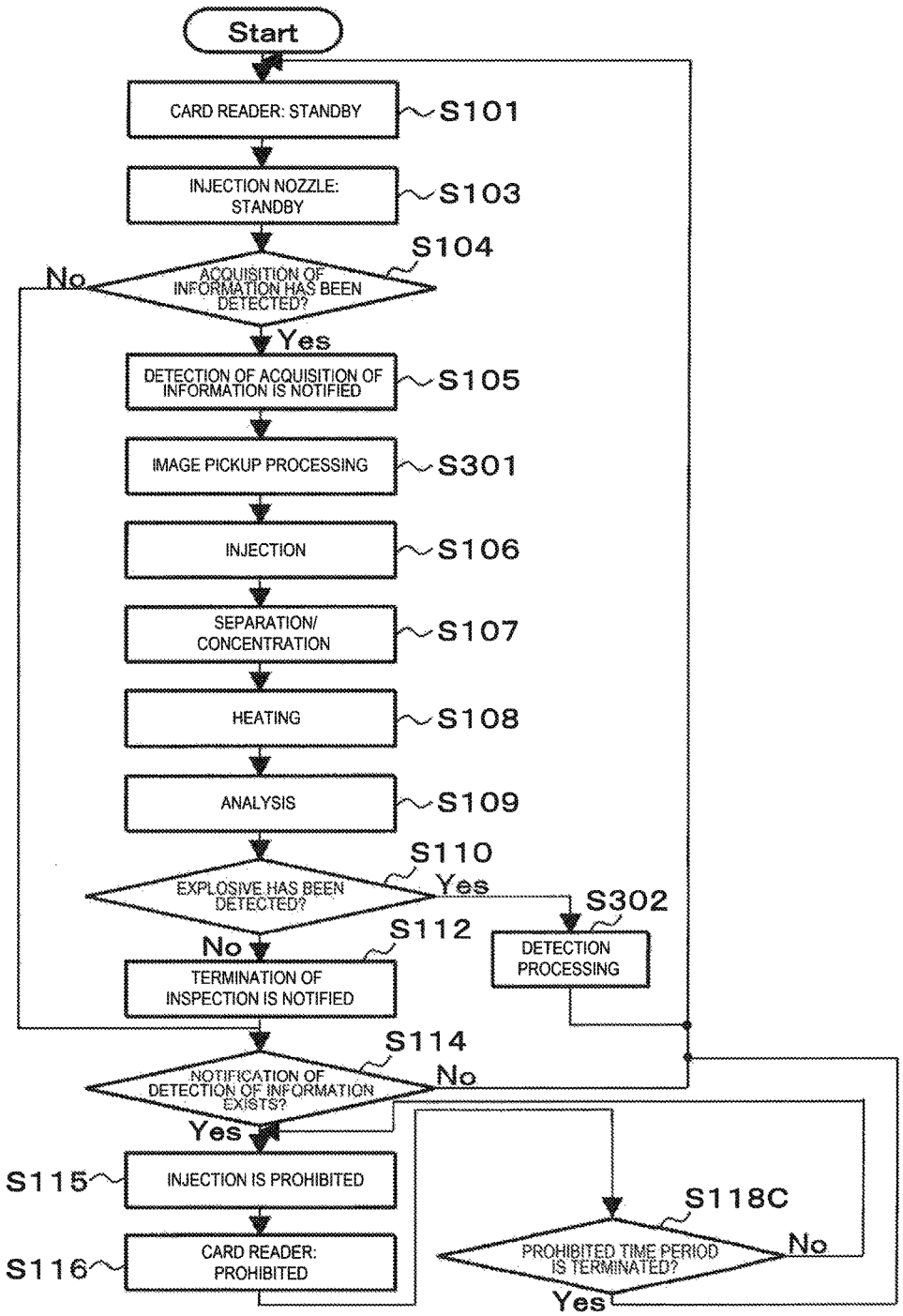
[FIG. 21]

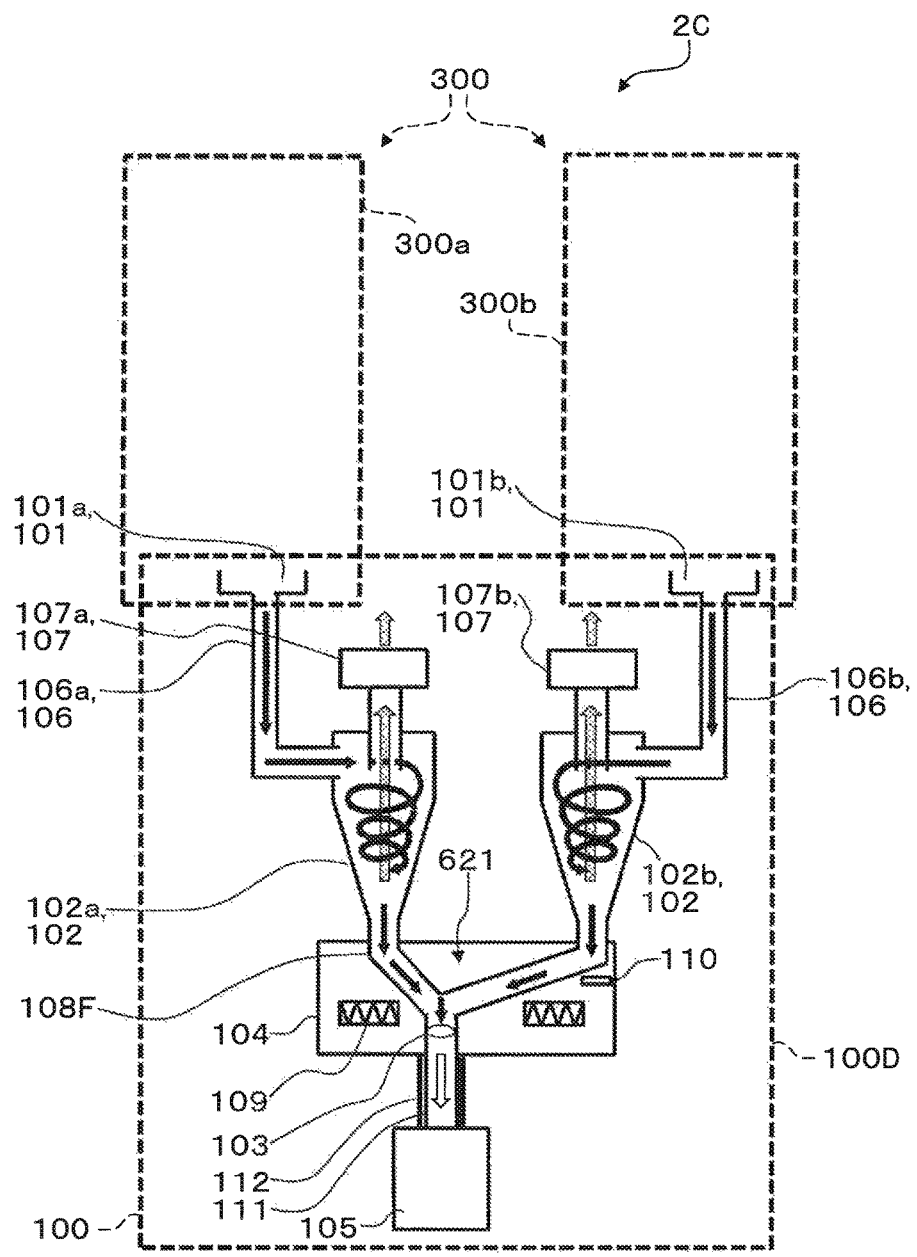
[FIG. 22]

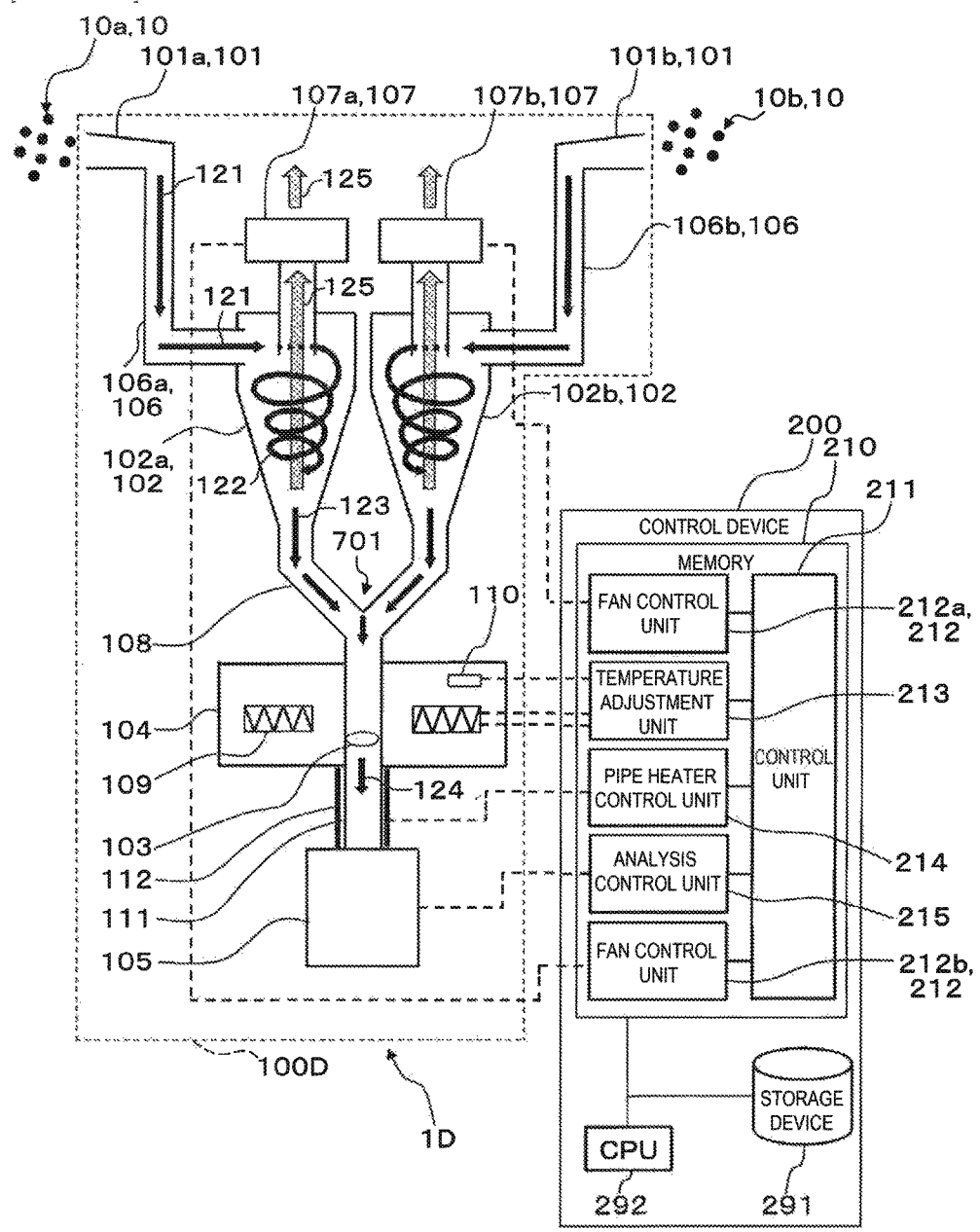
[FIG. 24]

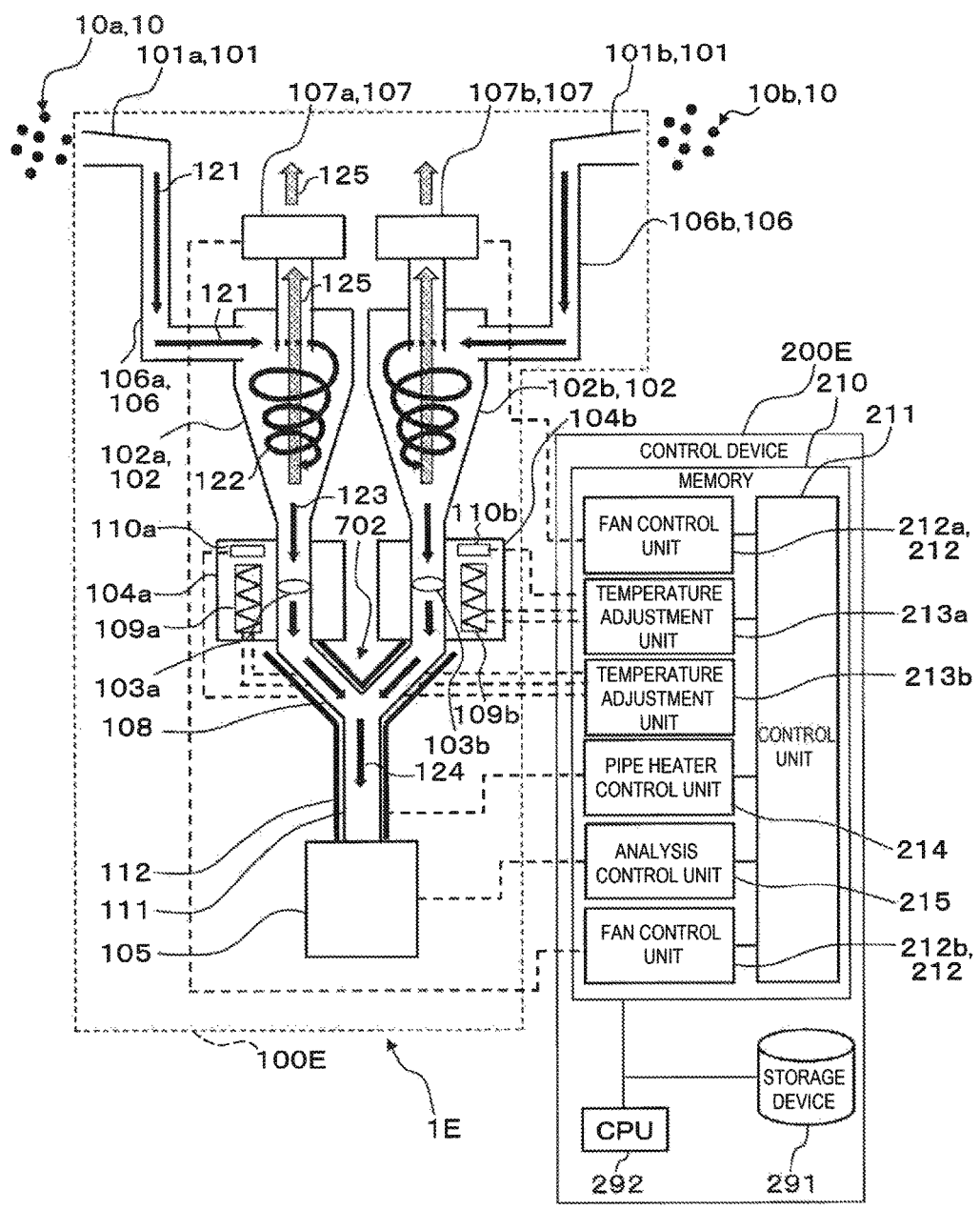
[FIG. 25]

SUBSTANCE-TESTING APPARATUS, SUBSTANCE-TESTING SYSTEM, AND SUBSTANCE-TESTING METHOD

TECHNICAL FIELD

The present invention relates to a technique of a substance testing apparatus, a substance testing system, and a substance testing method for collecting and analyzing particles.

BACKGROUND ART

A technique disclosing a technique that aims at ensuring safety/security in public facilities such as an airport and a harbor is, for example, a technique disclosed in PTL 1. PTL 1 discloses an explosive detection screening apparatus for detecting particles or vapor of the particles in order to detect dangerous/hazardous substances such as explosives, chemical reagents, narcotic drugs, and anesthetics.

CITATION LIST

Patent Literature

PTL 1: JP-A-9-126966

SUMMARY OF INVENTION

Technical Problem

When a particle testing system such as an explosive detection screening apparatus for detecting explosives, drugs, and the like is placed in public facilities or the like, for example, the following problems mainly arise: ensuring a practical processing speed; ensuring an installation space; and costs of introduction and maintenance/management.

The practical processing speed needed in such a particle testing system changes depending on public facilities or the like in which the particle testing system is installed and cannot be unconditionally determined. However, for example, the following value is needed, considering that the particle testing system is used together with an existing security system in an airport, a harbor, or the like. That is, in the case of, for example, a security gate in which a target to be inspected is a person, about 3 seconds/person is needed as a processing speed for each gate. In the case where the particle testing system is used for baggage testing or luggage testing in a back office, the processing speed greatly depends on an testing form thereof but is required to be substantially equal to or more than the processing speed of the security gate in some cases.

Regarding the installation space for the particle testing system, for example, the following point is considered. For example, assuming that the particle testing system is installed in an existing security gate or the like for use in public facilities, it is considered that the particle testing system is used together with existing security systems such as an X-ray testing apparatus and a metal detector. Therefore, the particle testing system needs to be installed in a footprint substantially equal to a footprint of the existing security gate.

Regarding the costs of introduction and maintenance of the particle testing system, as a matter of course, it is preferable that the costs be reduced as much as possible. Recently, various kinds of security equipment have been introduced also in comparatively safe countries in order to prevent terrorism and the like. Thus, the burden of the costs for introducing, maintaining, and managing the security equipment is increased. In particular, in airports, harbors, railroads, and the like, it is necessary to install and operate a plurality of particle testing systems for the purpose of ensuring convenience and maintaining redundancy of the system. Therefore, necessity for cost reduction is high. Further, when the costs related to introduction and maintenance are low, the particle testing system can be used in more facilities or the like, and therefore there is a high potential demand for cost reduction.

However, inmost analysis apparatuses for detecting particle components, which are used in the particle testing systems, it is difficult to reduce manufacturing costs and maintenance/management costs because of a principle structure thereof or in order to maintain a detection property thereof.

It is considered that, as means for solving the above problems, for example, selection means such as a mechanical switching valve is provided at a subsequent stage of collection ports of particles. Such a particle testing system can obtain, with a single analysis apparatus, the same effect as when particles obtained from a plurality of particle testing systems are analyzed. In other words, particles can be collected through a plurality of particle collection ports at different timings by selection means of the particle collection ports and can be analyzed, and therefore it is possible to obtain the same effect as when particles obtained from a plurality of particle testing systems are analyzed.

Generally, it is difficult to match conductance (ease of passing of particles) of a plurality of long pipes at a high level. Therefore, provision of the selection means such as the mechanical switching valve at the subsequent stage of the particle collection ports is good means that can eliminate variation caused by a difference in conductance between the pipes from the collection ports of particles to the analysis apparatus. However, in such a particle testing system, at least the following new problems arise and cannot be easily solved.

(1) In the case where the mechanical switching valve or the like is used as the selection means, a dead volume is generated due to a structure thereof. Further, it is difficult for the switching valve to completely separate particles obtained from different collection ports, and therefore contamination such as absorption and stagnation of vapor components cannot be eliminated.

(2) In analysis of particles, the particles are heated and the particles are vaporized. Further, it is necessary to prevent condensation of components of the particles vaporized for analysis. Therefore, it is necessary to constantly heat and keep the particle analysis system at about 200° C. In addition, the particle analysis system is heated to a higher temperature at the time of cleaning treatment such as baking. Therefore, in the case where the mechanical switching valve is used as the selection means, the switching valve itself is required to have a high heat-resisting property, and thus, for example, it is difficult to prevent deterioration of a seal portion of the switching valve and to maintain durability of operation components.

(3) In order to maintain the practical processing speed of testing, it is necessary to perform switching at a high speed in seconds or less. Because the particle analysis system is constantly heated and kept at a high temperature as described above, the selection means needs to have both the heat-resisting property and the durability. However, it is difficult to have both the heat-resisting property and the durability as described above.

(4) In the case where the switching valve or the like is used as the selection means, friction powder of a sealing material generated in accordance with operation, abrasion powder generated from a sliding unit in accordance with operation, gas components generated from members themselves constituting the switching valve, and the like cause contamination and clogging of a filter. Therefore, in such a particle analysis system, it is difficult to perform stable operation and maintain analysis accuracy for a long time.

PTL 1 discloses a sample collector and an evaporator for collecting a particle sample from an airflow and evaporating the particle sample. The sample collector and the evaporator in the technique disclosed in PTL 1 collect and evaporate particles by rotationally moving three filter elements placed on a circular plate to a collection chamber, to an evaporation chamber, and to a cleaning chamber. In such a mechanism, it is difficult to achieve the practical processing speed, which is one of the problems to be solved by the invention. Further, the sample collector and the evaporator in the technique disclosed in PTL 1 need to rotate the circular plate in order to evaporate particles, and therefore mechanical switching means is needed. Thus, for the reasons mentioned above, the technique disclosed in PTL 1 cannot solve the above problems.

The invention has been made in view of the above background, and an object of the invention is to save a space for an apparatus for inspecting a substance and reduce a cost thereof.

Solution to Problem

In order to solve the above problems, the invention includes: a plurality of collection units for collecting substances to be inspected; concentration units for concentrating the substances collected in the collection units, the concentration units being connected to the respective collection units in pairs; and a common analysis unit for acquiring the concentrated substances from the concentration units and analyzing the substances, the analysis unit being connected to the concentration units.

Advantageous Effects of Invention

According to the invention, it is possible to save a space for an apparatus for inspecting a substance and reduce a cost thereof.

BRIEF DESCRIPTION OF DRAWINGS

FIG. 1 illustrates a configuration example of a particle testing system according to Embodiment 1.

FIG. 2 illustrates an external appearance example of a security gate system according to Embodiment 2.

FIG. 3 illustrates apart of an A-A cross-section of a security gate.

FIG. 4 illustrates a detailed configuration example of the security gate system according to Embodiment 2.

FIG. 5 illustrates a configuration example of a control apparatus according to Embodiment 2.

FIG. 6 is a flowchart showing an operation procedure of the security gate system according to Embodiment 2.

FIG. 7 is a flowchart showing an operation procedure of a security gate system according to Embodiment 3.

FIG. 10 illustrates a detailed configuration example of a security gate system according to Embodiment 4.

FIG. 11 shows a configuration example of a control apparatus according to Embodiment 4.

FIG. 12 illustrates a configuration example of arrangement of line sensors.

FIG. 13 illustrates a configuration example of arrangement of injection nozzles.

FIG. 14 is a (first) flowchart showing a processing procedure in the security gate system according to Embodiment 4.

FIG. 15 is a (second) flowchart showing a processing procedure in the security gate system according to Embodiment 4.

FIG. 16 illustrates an external appearance example of a security station according to Embodiment 5.

FIG. 17 illustrates a (first) detailed configuration example of the security station according to Embodiment 5.

FIG. 18 illustrates a (second) detailed configuration example of the security station according to Embodiment 5.

FIG. 19 illustrates a configuration example of a control apparatus according to Embodiment 5.

FIG. 20 is a (first) flowchart showing an operation procedure of the security station according to Embodiment 5.

FIG. 21 is a (second) flowchart showing an operation procedure of the security station according to Embodiment 5.

FIG. 22 illustrates a configuration example of a security gate system according to Embodiment 6.

FIG. 24 illustrates a configuration example of a particle testing system according to Embodiment 7.

FIG. 25 illustrates a configuration example of a particle testing system according to Embodiment 8.

DESCRIPTION OF EMBODIMENTS

Figure 8A:
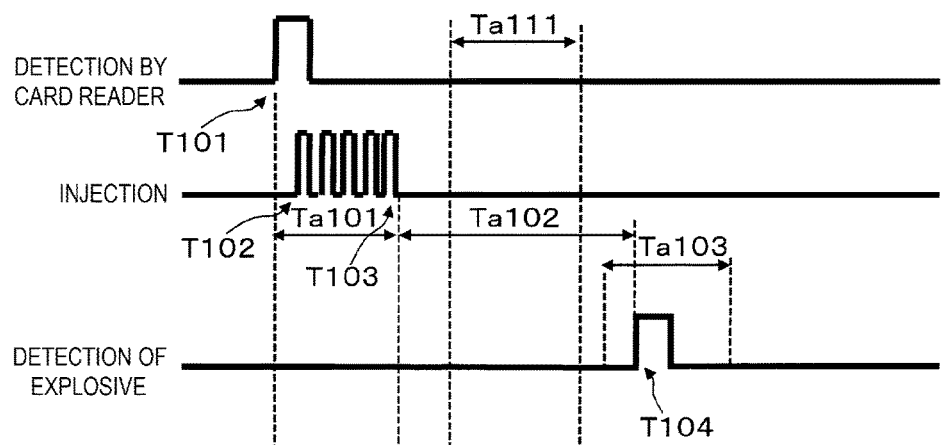
FIGS. 8A and 8B show examples of operation time charts in the security gate system according to Embodiment 3.

Forms for implementing the invention (referred to as "embodiments") will be described in detail with reference to the drawings as appropriate. Note that, in the drawings, similar constituent elements are denoted by the same reference signs, and description thereof is omitted.

In the embodiments, it is assumed that particles to be detected are explosive particles or particles resulted from an explosive substance. However, the particles to be detected are not limited thereto. For example, the particles to be detected may be explosive substances, drugs such as stimulant drugs, chemical substances that affect a human body (for example, pesticide), particles resulted from dangerous substances and the like which are generally considered to affect a human body, microorganisms such as bacteria that affect a human body, and viruses.

[Embodiment 1]

(System Configuration)

FIG. 1 illustrates a configuration example of a particle testing system according to Embodiment 1.

A particle testing system (substance testing system) 1 includes a particle testing apparatus (substance testing apparatus) 100 and a control apparatus 200.

The particle testing apparatus 100 has the following configuration.

Collection ports (collection units) 101 (101a and 101b) collect particles (substances) 10 (10a and 10b) serving as a target to be detected and introduce the collected particles 10 (10a and 10b) into introduction pipes 106 (106a and 106b).

Cyclone centrifuges (hereinafter, referred to as centrifuges 102 (102a and 102b)) serving as concentration units concentrate and separate the introduced particles 10 (10a and 10b). The centrifuges 102a and 102b are connected to the respective collection ports 101a and 101b in pairs.

Note that, although the particle testing apparatus 100 according to this embodiment will be described by using the cyclone centrifuge as an example of means for concentrating and separating the introduced particles 10, an impactor or the like may be used instead of the cyclone centrifuge. The impactor separates the particles 10 from an airflow by using an inertia effect or separates the particles 10 from an airflow by electrifying the particles 10. After separating the particles 10, the impactor concentrates the particles 10 by using concentration means or applying a dust collection technique using static electricity.

A heating block 104 includes a heating filter (heating unit) 103 for heating and vaporizing the particles 10 concentrated and separated in the centrifuges 102. The heating block 104 also includes heating heaters 109 for heating the heating filter 103 and a temperature sensor 110 for detecting a temperature of the heating block 104. As illustrated in FIG. 1, the single heating filter 103 is provided on an analysis apparatus 105 side from a point at which the particles 10a and 10b sent from the respective centrifuges 102a and 102b are merged. Note that a part in which the heating filter 103 is provided does not need to be limited to the analysis apparatus 105 side from the point at which the particles 10a and 10b sent from the respective centrifuges 102a and 102b are merged.

Note that, although the heating filter 103 is used as an example of means for heating and vaporizing the particles 10 in this embodiment, the means is not limited thereto. For example, instead of the heating filter 103, a resistance heating heater for generating heat by applying a current or voltage may be used, or heating means obtained by combining a lamp heater using infrared radiation, ultraviolet radiation, or the like with a filter may be used. Further, means for directly heating the particles 10 with the use of a lamp heater using infrared radiation, ultraviolet radiation, or the like to vaporize the particles 10 or other means may also be used.

Herein, the collection port 101a is connected to the centrifuge 102a via the introduction pipe 106a (106), and the collection port 101b is connected to the centrifuge 102b via the introduction pipe 106b (106). Further, exhaust fans 107 (107a and 107b) for generating a cyclone phenomenon are provided in the centrifuges 102 (102a and 102b), respectively.

The heating block 104 is connected to the centrifuges 102a and 102b via a branch pipe 108 that is connected to the centrifuges 102a and 102b and has branched portions merged in the heating block 104. In Embodiment 1, the heating filter 103 is installed on a downstream side of a position at which the branched portions of the branch pipe 108 extending from the respective centrifuges 102a and 102b are merged. Note that, herein, the side of the collection ports 101 is defined as an upstream, and the side of the analysis apparatus 105 is defined as a downstream.

The branch pipe 108 is connected to the analysis apparatus 105 via a pipe 111. On an outer circumference of the pipe 111, a pipe heater 112 for preventing a component of the vaporized particles 10 from condensing on the inside thereof is provided. The pipe 111 is (constantly) heated and kept warm by the pipe heater 112.

The analysis apparatus (analysis unit) 105 is a apparatus for analyzing the particles 10 vaporized in the heating block 104 to analyze a component of the particles 10. As illustrated in FIG. 1, the analysis apparatus 105 is used by the centrifuges 102a and 102b in common.

The analysis apparatus 105 can be, for example, an ion trap mass spectrometer using a difference in mass of a substance, an ion-mobility mass spectrometer using a difference in mobility of ions, a quadrupole mass spectrometer using a mass-to-charge ratio of the particles 10, or a magnetic sector mass spectrometer using a difference in path on which ions pass through a homogeneous magnetic field. Note that, in this embodiment, a vapor component derived from the particles 10 is a target to be analyzed, and therefore it is assumed that the analysis apparatus 105 includes a vacuum pump or the like which can perform negative pressure suction so that the analysis apparatus 105 can suck the vapor component of the particles 10 serving as the target to be analyzed. The analysis apparatus 105 does not necessarily need to be a general-purpose analysis apparatus 105 and may be a simplified analysis apparatus 105 specialized for detecting a vapor component derived from specific particles 10.

Herein, lengths from the centrifuges 102a and 102b to the analysis apparatus 105 are the same length in terms of conductance.

The control apparatus 200 controls each unit of the particle testing apparatus 100.

The control apparatus 200 includes fan control units 212 (212a and 212b), a temperature adjustment unit 213, a pipe heater control unit 214, and an analysis control unit 215 and further includes a control unit 211 for controlling the units 212 to 215.

The control unit 211 and the units 212 to 215 are realized in such a way that programs stored in a storage apparatus 291 are loaded into a memory 210 and are executed by a CPU (Central Processing Unit) 292.

The fan control units 212 (212a and 212b) control the respective exhaust fans 107 (107a and 107b).

The temperature adjustment unit 213 controls a temperature of the heating heaters 109 on the basis of temperature information obtained from the temperature sensor 110, thereby controlling a temperature of the heating block 104.

The pipe heater control unit 214 controls a temperature or heat generation amount of the pipe heater 112.

The analysis control unit 215 receives an analysis result of particles from the analysis apparatus 105 and, for example, determines whether or not the particles are an explosive on the basis of the analysis result.

Note that the control apparatus 200 and the particle testing apparatus 100 may be integrally provided.

(Processing)

A procedure in which the particle testing apparatus 100 detects and analyzes the particles 10 will be described.

Herein, a procedure in which particles 10a collected into the collection port 101a are detected will be described, and description of the procedure in which the particles 10b collected into the collection port 101b are detected is omitted. This is because a procedure in which particles 10b collected into the collection port 101b are detected is the same as the procedure in which the particles 10a collected into the collection port 101a are detected.

First, the particles 10a serving as a target to be detected are peeled off by some means from an object to which the particles adhere, are conveyed in the vicinity of the collection port 101*a*, and are collected into the collection port 101*a*. A method for peeling off the particles 10*a* from the object will be described later.

Then, the particles 10*a* collected into the collection port 101*a* are introduced together with a large amount of air by an airflow generated by the exhaust fan 107*a* from the collection port 101*a* into the centrifuge 102*a* through the introduction pipe 106*a*.

Note that a flow of the air containing the particles 10*a* is indicated by an arrow 121 in FIG. 1. The particles 10*a* introduced into the centrifuge 102*a* are concentrated by separating the particles from the large amount of air with a principle of centrifugation called cyclone phenomenon.

That is, in the centrifuge 102*a*, the flow 121 of the air containing the particles 10*a* falls while being rotated by a rotating airflow 122 of the centrifuge 102*a* along an inner wall of a cylindrical portion.

At this time, at the center of the centrifuge 102*a*, a central pressure is reduced by an influence of a centrifugal force and an updraft 125 is generated accordingly, and the large amount of air is exhausted by this updraft 125 through the exhaust fan 107*a* to the outside of the centrifuge 102*a*.

On the inside of the centrifuge 102*a* in which the rotating airflow 122 is generated, the particles 10*a* having a large mass are separated outward to collide with an inner wall surface and therefore lose a kinetic energy. The particles 10*a* that have lost the kinetic energy are precipitated downward along the wall surface, and, as a result, the particles 10*a* are separated from the large amount of air.

In this way, the centrifuge 102*a* separates the particles 10*a* from the air and concentrates the particles 10*a*.

The particles 10*a* separated from the air by the centrifuge 102*a* pass through the branch pipe 108 to reach the heating filter 103 in the heating block 104 because of an influence of gravity and an influence of suction from the analysis apparatus 105 (arrow 123).

The heating filter 103 is heated and kept at a temperature suitable for heating and evaporating (vaporizing) the particles 10*a* to be analyzed. The particles 10*a* are, for example, brought into contact with the heating filter 103, and therefore a vapor component is generated from the particles 10*a*. The generated vapor component passes through the pipe 111 to be introduced into the analysis apparatus 105 because of the influence of suction of the analysis apparatus 105 (arrow 124).

At this time, when a temperature of an inner wall of the pipe 111 is low, the vapor component of the particles 10*a* is condensed on the inner wall of the pipe 111 by a phenomenon called cold spot. In order to avoid this problem, the pipe 111 is heated and kept at substantially the same temperature as a temperature of the heating filter 103 by the pipe heater 112 as described above.

Then, the vapor component of the particles 10*a* is analyzed by the analysis apparatus 105. For example, in the case where a mass spectrometer is used as the analysis apparatus 105, the component of the particles 10*a* is analyzed by comparing a profile of a detected substance with a profile of data of an explosive input in advance. An analysis result is transmitted to the control apparatus 200.

A size of the particles 10 separated in the centrifuge 102 is determined on the basis of a shape of a cyclone and an inlet flow rate in the centrifuge 102, and therefore, when the centrifuge 102*a* and the centrifuge 102*b* are similar centrifuges 102, the single particle testing apparatus 100 can collect and analyze the particles 10 that is double the amount of particles collected and analyzed by a conventional particle testing apparatus. On the contrary, in the case where the centrifuge 102*a* and the centrifuge 102*b* have different shapes and inlet flow rates, the particles 10 separated and concentrated by the centrifuges 102*a* and 102*b* have different sizes. Therefore, a plurality of kinds of particles 10 can be selectively collected.

In this embodiment, in the case where the particles 10 having several nanograms to several micrograms are collected into the collection ports 101, it is possible to analyze the particles 10 in about 3 seconds or less, depending on the kinds of the particles 10.

(Effects of Embodiment 1)

The particle testing system 1 according to this embodiment has the following effects.

(1) The particles 10 introduced through both the collection ports 101 (101*a* and 101*b*) are separately separated and concentrated in the individual centrifuges 102 (102*a* and 102*b*). Thus, the particle testing apparatus 100 according to this embodiment can have a function corresponding to a plurality of general particle testing apparatuses with the use of the single analysis apparatus 105 without losing efficiency of concentration and collection of the particles 10 at all. With this, it is possible to save a space for the particle testing apparatus 100 according to this embodiment.

(2) The particle testing apparatus 100 according to this embodiment includes only a comparatively expensive single analysis apparatus 105. Therefore, the particle testing apparatus 100 according to this embodiment can have a function similar to a function of a plurality of general particle testing apparatuses with a cost of the single analysis apparatus 105. That is, it is possible to improve cost performance.

(3) In the particle testing apparatus 100 according to Embodiment 1, the centrifuges 102 can be independently installed with respect to the collection ports 101. That is, a single collection port 101 is provided for each centrifuge 102. Therefore, the particle testing apparatus 100 according to this embodiment does not lose a classification property of the sizes or the like of the particles 10 to be concentrated in the individual centrifuges 102 at all. In addition, the particle testing apparatus 100 according to Embodiment 1 can have a function similar to a function of a plurality of general particle testing apparatuses with the use of the single analysis apparatus 105 without losing the classification property of the sizes or the like of the particles 10 to be concentrated at all.

(4) The particle testing apparatus 100 according to this embodiment can connect a plurality of collection apparatuses with the single analysis apparatus 105 without using a physical switching mechanism. Therefore, the particle testing apparatus 100 according to this embodiment can have, for example, all the following points: improvement in a processing capacity per time unit; high durability; and a maintenance-free property for a long time.

Further, the heating filter 103 is provided on a downstream side of the merged part in the branch pipe 108, and therefore the particle testing apparatus 100 can be used as a mass spectrometer. In addition, because the heating filter 103 is provided on the downstream side of the merged part in the branch pipe 108, it is only necessary to provide the single heating filter 103. With this, cost reduction can be achieved.

[Embodiment 2]

Embodiment 2 of the invention will be described. In Embodiment 2, a security gate system 2A (FIG. 4) to which the particle testing system 1 in Embodiment 1 is applied will be described.

(External Appearance)

FIG. 2 illustrates an external appearance example of the security gate system according to Embodiment 2.

A security gate includes particle peeling-off units (peeling-off units) 301 (301a and 301b), card readers 302 (302a and 302b), collection ports 101 (101a and 101b), and a gate flap 303 (303b). Note that, although another gate flap exists on an opposite side of the gate flap 303b, the gate flap is not illustrated in FIG. 2.

The particle peeling-off units 301 (301a and 301b) peel off particles from an IC (Integrated Circuit) card (information recording medium) or the like possessed by a target person 20 serving as a target to be inspected.

The card readers 302 (302a and 302b) read information such as ID (Identification) from the IC card or the like.

The collection ports 101 (101a and 101b), as well as the collection ports 101 (101a and 101b) illustrated in FIG. 1, collect the particles peeled off from the IC card or the like.

The gate flap 303 (303b) closes when the particle testing system detects an explosive. In this embodiment, it is assumed that the gate flap 303 is normally closed and opens when the particle testing system does not detect the explosive. However, the gate flap 303 is not limited thereto, and the gate flap 303 that is normally open and closes when the particle testing system detects the explosive may be used. Alternatively, another gate flap may be used.

In this example, the target person 20 passes through a security gate 300 in a direction indicated by an arrow. When the target person 20 passes through the security gate 300, the security gate 300 reads information from the IC card or the like and collects particles from the IC card or the like. A particle testing system 1A (FIG. 4) determines whether or not the collected particles are an explosive.

(Peeling Off Method)

FIG. 3 illustrates a part of an A-A cross-section of the security gate illustrated in FIG. 2.

A method of peeling off and collecting particles 10a adhering to an IC card 30 will be described with reference to FIG. 3. A method of peeling off particles with the use of the particle peeling-off unit 301a will be described herein, but a method of peeling off particles with the use of the particle peeling-off unit 301b is similar to the method using the particle peeling-off unit 301a, and therefore description regarding the particle peeling-off unit 301b is omitted.

As illustrated in FIG. 3, the particle peeling-off unit 301a includes a compressed air injection nozzle (hereinafter, referred to as an injection nozzle 311a) serving as a peeling-off unit.

When the target person 20 (FIG. 2) causes the IC card 30 to approach the card reader 302a, the card reader 302a detects the approach of the IC card 30 and reads information from the IC card 30 in a non-contact manner.

Then, at the same time when the information is acquired by the card reader 302a or immediately after the information is acquired, pulsed compressed air is injected from the injection nozzle 311a of the particle peeling-off unit 301a for a certain time period. In this way, the particles 10a adhering to a surface of the IC card 30 are peeled off by the compressed air injected from the injection nozzle 311a.

An injection pressure desirably has, for example, about 0.05 MPa to 0.1 MPa. Further, the injection nozzle 311a desirably injects compressed air with a frequency of about 1 to 5 times/second, but the injection pressure and the injection frequency are not limited to the above injection pressure and injection frequency.

The particles 10a peeled off from the IC card 30 are transferred in a direction of the collection port 101a by an airflow generated by the compressed air injected by the injection nozzle 311a and are collected by the collection port 101a.

As described above, the substance peeling-off unit 301 is provided in the vicinity of the collection port 101, and therefore it is possible to securely collect the particles 10 adhering to a target to be inspected.

Further, the card reader 302 is placed in the vicinity of the collection port 101, and therefore it is possible to read information of the IC card 30 and collect the particles 10a derived from the IC card 30 at the same time.

(System Configuration)

FIG. 4 illustrates a detailed configuration example of the security gate system according to Embodiment 2.

A difference from FIG. 1 will be described with reference to FIG. 4, and configurations similar to those in FIG. 1 are denoted by the same reference signs, and description thereof is omitted.

The security gate system (substance testing system) 2A illustrated in FIG. 4 includes two security gates 300a and 300b (300) and the particle testing system 1A.

The security gates 300a and 300b include the card readers 302 (302a and 302b) and the gate flaps 303 (303a and 303b).

The injection nozzles 311 (311a and 311b) constituting the particle peeling-off units 301 (FIG. 2, FIG. 3) have already been described with reference to FIG. 2 and FIG. 3, and therefore description thereof is omitted herein.

Note that, reference signs 321 (321a and 321b) illustrated in FIG. 4 denote electromagnetic valves for controlling injection from the injection nozzles 311 (311a and 311b) and constitute the particle peeling-off units 301 (301a and 301b) (FIG. 2, FIG. 3).

A control apparatus 200A will be described later.

A configuration of a particle testing apparatus 100 is similar to the configuration thereof in Embodiment 1, and therefore description thereof is omitted herein.

FIG. 5 illustrates a configuration example of the control apparatus according to Embodiment 2. Note that, in FIG. 5, elements similar to elements in FIG. 1 are denoted by the same reference signs, and description thereof is omitted.

The control apparatus 200A includes not only the configurations of the control apparatus 200 illustrated in FIG. 1 but also card reader control units 221 (221a and 221b), injection nozzle control units 222 (222a and 222b), and gate flap control units 223 (223a and 223b).

The card reader control units 221 (221a and 221b) control reading of information using the card readers 302 (302a and 302b).

The injection nozzle control units 222 (222a and 222b) control the electromagnetic valves 321 (321a and 321b) in the injection nozzles 311 (311a and 311b) to control the injection frequency and the number of injection times of pulsed compressed air injected from injection nozzles 311.

The gate flap control units 223 (223a and 223b) control opening/closing of the gate flaps 303 (303a and 303b).

A control unit 211A controls the units 212 to 215 and 221 to 223.

Note that the control unit 211A and the units 212 to 215 and 221 to 223 are realized in such a way that programs stored in a storage apparatus 291 are loaded into a memory 210 and are executed by a CPU 292.

(Flowchart)

FIG. 6 is a flowchart showing an operation procedure of the security gate system according to Embodiment 2. FIG. 2 to FIG. 5 are referred to as appropriate.

The security gate system 2A according to this embodiment exclusively operates the two security gates 300a and 300b in accordance with the flowchart shown in FIG. 6. With this, it is possible to specify which one of the security gates 300a and 300b detects an explosive.

Although processing in the security gate 300a will be mainly described with reference to FIG. 6, similar processing is also performed in the security gate 300b.

First, the card reader control unit 221a of the control apparatus 200A causes the card reader 302a of the security gate 300a to be in a standby state (S101). At this time, for example, the card reader control unit 221a displays a display portion (not illustrated) of the card reader 302a in "blue" indicating a standby state.

Further, the gate flap control unit 223a causes the gate flap 303a to stand by in a "closed" state (S102).

Furthermore, the injection nozzle control unit 222a causes the injection nozzle 311a to be in a standby state by controlling the electromagnetic valve 321a of the injection nozzle 311a (S103).

Then, the card reader control unit 221a determines whether or not acquisition of information has been detected in the card reader 302a (S104).

As a result of Step S104, in the case where the card reader control unit 221a has not detected the acquisition of the information (S104→No), the control unit 211A advances processing to Step S114.

As a result of Step S104, in the case where the card reader control unit 221a has detected the acquisition of the information (S104→Yes), the card reader control unit 221a notifies the control unit 211A that acquisition of information of the IC card 30 has been detected in the security gate 300a (S105).

Note that detection of the acquisition of the information in Step S104 also means that the control apparatus 200A has detected collection of the particles 10a in the collection port 101a.

After the acquisition of the information is detected in Step S104, the card reader control unit 221a may prohibit operation of the card reader 302a. Similarly, the injection nozzle control unit 222a may prohibit operation of the injection nozzle 311a. Furthermore, the gate flap control unit 223a may prohibit operation of the gate flap 303a.

Then, the injection nozzle control unit 222a injects compressed air from the injection nozzle 311a (S106). By injecting the compressed air from the injection nozzle 311a, the particles 10a are peeled off from the IC card 30.

Then, the particles 10a peeled off from the IC card 30 are collected by the collection port 101a and are transferred to the centrifuge 102a.

The centrifuge 102a centrifuges the transferred particles 10a, thereby separating the particles 10a from air to concentrate the particles 10a (S107).

The separated and concentrated particles 10a are, for example, brought into contact with the heating filter 103 in the heating block 104 and are therefore heated (S108) to be vaporized.

Then, the analysis apparatus 105 analyzes the vaporized particles 10a (S109).

The analysis apparatus 105 transmits an analysis result to the control apparatus 200A, and the analysis control unit 215 of the control apparatus 200A determines whether or not an explosive has been detected (S110).

As a result of Step S110, in the case where an explosive has been detected (S110→Yes), the control unit 211A performs detection processing (S111) and returns the processing to Step S101. In the detection processing, for example, the gate flap control unit 223a of the control apparatus 200A closes the gate flap 303a and causes a security system (not illustrated) to issue a warning. At this time, the control unit 211A associates the information of the IC card 30 read by the card reader 302a with a result of detection of the explosive and causes the security system (not illustrated) to issue a warning. That is, the control unit 211A associates the analysis result in the analysis apparatus 105 with the information read from the IC card 30. Note that association of the analysis result in the analysis apparatus 105 with the information read from the IC card 30 may be performed regardless of detection/non-detection of the explosive.

With this, the target person 20 (FIG. 2) who possesses the explosive can be easily specified.

When the control unit 211A returns the processing to Step S101 after the detection processing in Step S111 is terminated, the security gate system 2A continues normal processing even in the case where the explosive has been detected. With this, it is possible to catch the target person 20 (FIG. 2) who possesses the explosive at a safe place while such detection of the explosive is not being noticed by the person.

Note that, in the case where it is desirable to catch the target person 20 who possesses the explosive immediately, the control unit 211A may terminate the processing after Step S111.

As a result of Step S110, in the case where no explosive has been detected (S110→No), the control unit 211A notifies the card reader control unit 221b, the injection nozzle control unit 222b, and the gate flap control unit 223b of the security gate 300b that testing in the security gate 300a has been terminated (S112).

Then, the gate flap control unit 223a causes the gate flap 303a to be in an "open" state (S113).

Then, the control unit 211A determines whether or not notification of acquisition of information of the IC card 30 has been received from the card reader control unit 221b of the security gate 300b (S114). This notification has been transmitted in Step S105 in the security gate 300b.

As a result of Step S114, in the case where the notification of the acquisition of the information of the IC card 30 has not been received from the security gate 300b (S114→No), the control unit 211A returns the processing to Step S101.

As a result of Step S114, in the case where the notification of the acquisition of the information of the IC card 30 is received from the security gate 300b (S114→Yes), the injection nozzle control unit 222a prohibits injection of compressed air using the injection nozzle 311a (S115).

Then, the card reader control unit 221a prohibits the card reader 302a of the security gate 300a from reading (S116). At this time, for example, the card reader control unit 221a displays the display portion (not illustrated) of the card reader 302a in the security gate 300a in "red" indicating a prohibited state.

Further, the gate flap control unit 223a causes (prohibits) the gate flap 303a to be in an open prohibited state (S117).

By the processing in Steps S115 to S117, the collection port 101a is prohibited from collecting the particles 10a.

Then, the control unit 211A determines whether or not notification of termination of testing has been received from the security gate 300b (S118). This notification has been transmitted in Step S112 in the security gate 300b.

As a result of Step S118, in the case where the notification of the termination of the testing has not been received from the security gate 300b (S118→No), the control unit 211A returns the processing to Step S115.

As a result of Step S118, in the case where the notification of the termination of the testing is received from the security gate 300b (S118→Yes), the control unit 211A returns the processing to Step S101. That is, the control unit 211A cancels prohibition of injection using the injection nozzle 311a, prohibition of reading of information using the card reader 302a, and the open prohibited state (prohibition) of the gate flap 303a. This is performed to prevent the particles 10a collected in the security gate 300a from being mixed with the particles 10b collected in the security gate 300b.

According to Embodiment 2, it is possible to authenticate the IC card 30 or the like and inspect the particles 10 adhering to the IC card 30.

Further, for example, when the security gate 300a detects acquisition of information from the IC card 30, the security gate system 2A according to Embodiment 2 stops operation of the card reader 302b and the injection nozzle 311b in the security gate 300b until testing of the particles in the security gate 300a is terminated, and vice versa. In this way, the security gate system 2A according to Embodiment 2 can specify which one of the security gates 300 has acquired the particles 10 serving as a target to be inspected.

Further, the security gate system 2A according to this embodiment has the same length from the centrifuges 102a and 102b to the analysis apparatus 105. With this, the particles 10 acquired from the two security gates 300 are not mixedly analyzed even in the case where the security gate system 2A prohibits operation of the security gate 300 at the same time when acquisition of information from the IC card 30 is detected and cancels prohibition of the operation of the security gate 300 when analysis in the analysis apparatus 105 is terminated.

The security gate system 2A is applicable to entry/exit management in public facilities that perform authentication using the IC card 30 or the like, such as airports, harbors, ticket gates in stations, commercial facilities, office buildings, and amusement facilities.

[Embodiment 3]
(Flowchart)

FIG. 7 is a flowchart showing an operation procedure of a security gate system according to Embodiment 3.

Note that a configuration of a security gate system 2A according to Embodiment 3 is similar to the configurations illustrated in FIG. 2 to FIG. 5, and therefore description thereof is omitted herein.

In FIG. 7, processing similar to the processing shown in FIG. 6 is denoted by the same step numbers, and description thereof is omitted.

The processing shown in FIG. 7 is different from the processing shown in FIG. 6 in that, after Step S117, the control unit 211A determines whether or not a prohibited time period in the security gate 300a has been terminated (S118A). The prohibited time period is a time period in which operation of the injection nozzle 311a, the card reader 302a, and the gate flap 303a is prohibited after notification of acquisition of information is received from the security gate 300b. The prohibited time period is set to a certain time period in advance by a method described later.

As a result of Step S118A, in the case where the prohibited time period has not been terminated (S118A→No), the control unit 211A returns the processing to Step S115.

As a result of Step S118A, in the case where the prohibited time period is terminated (S118A→Yes), the control unit 211A returns the processing to Step S101.

(Prohibited Time Period)

In Embodiment 2 described above, for example, when the security gate 300a acquires information from the IC card 30, the security gate 300b prohibits operation of the injection nozzle 311b, the card reader 302b, and the gate flap 303b until testing of particles in the security gate 300a is completed.

On the contrary, in Embodiment 3, when the prohibited time period is terminated, prohibition of operation of the injection nozzle 311b, the card reader 302b, and the gate flap 303b is canceled even in the case where testing of particles in the security gate 300a that acquired information has not been completed.

Hereinafter, this will be described.

FIG. 8 shows examples of operation time charts in the security gate system according to Embodiment 3. FIG. 4 and FIG. 5 are referred to as appropriate.

FIG. 8(a) shows time charts of detection of acquisition of information using the card reader 302a, injection of compressed air from the injection nozzle 311a, and detection of an explosive derived from the security gate 300a in order from the top.

Figure 8B:
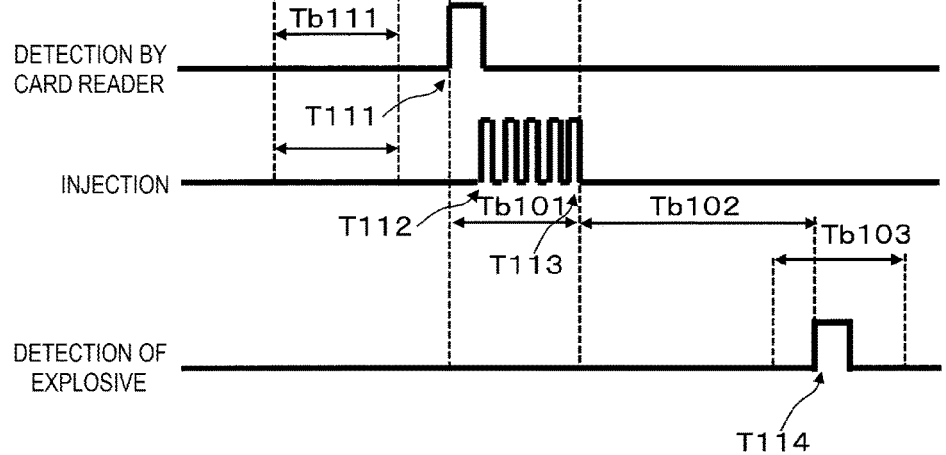

FIG. 8(b) shows time charts of detection of acquisition of information using the card reader 302b, injection of compressed air from the injection nozzle 311b, and detection of an explosive derived from the security gate 300b in order from the top.

When the card reader 302a recognizes the IC card 30 in the security gate 300a (time T101), pulsed compressed air is injected from the injection nozzle 311a in order to peel off particles 10 (time T102 to time T103). Thereafter, the analysis control unit 215 is assumed to detect an explosive derived from the security gate 300a at a time T104.

A time period between detection using the card reader 302a and termination of injection of compressed air using the injection nozzle 311a is defined as Ta101.

When the card reader 302a recognizes the IC card 30, operation of the card reader 302b and the injection nozzle 311b in the security gate 300b is prohibited. At this time, although not shown in FIG. 8, operation of the gate flap 303b is also prohibited (opening thereof is prohibited). A time period (prohibited time period) Tb111 in which the operation of the card reader 302b, the injection nozzle 311b, and the gate flap 303b is prohibited is a time period between the time T101 and the time T103, i.e., Ta101 in FIG. 8.

Similarly, when the card reader 302b recognizes the IC card 30 in the security gate 300b (time T111), pulsed compressed air is injected from the injection nozzle 311b in order to peel off the particles 10 (time T112 to time T113). Thereafter, the analysis control unit 215 is assumed to detect an explosive derived from the security gate 300b at a time T114.

A time period between detection using the card reader 302b and termination of injection of compressed air using the injection nozzle 311b is defined as Tb 101.

When the card reader 302b recognizes the IC card 30, operation of the card reader 302a and the injection nozzle 311a in the security gate 300a is prohibited. At this time, although not shown in FIG. 8, operation of the gate flap 303a is also prohibited (opening thereof is prohibited). A time period (prohibited time period) Ta111 in which the operation of the card reader 302a, the injection nozzle 311a, and the gate flap 303a is prohibited is a time period between the time T111 and the time T113, i.e., Tb101 in FIG. 8.

Herein, a time period after the injection of the compressed air using the injection nozzle 311a is terminated until the analysis control unit 215 detects an explosive is defined as an testing waiting time period Ta102. That is, the testing waiting time period Ta102 is the time T103 to the time T104. The testing waiting time period Ta102 changes depending on the kind of explosive particles 10 serving as a target to be inspected. For example, it is possible to predict that the testing waiting time period Ta102 is about 2 seconds in the case where the particles are TNT (Trinitrotoluene) particles and is about 5 seconds in the case where the particles are a military explosive or the like. Herein, a change in the detection time T104 in the security gate 300a is defined as an expected detection time period Ta103. The expected detection time period Ta103 is an expected time period required for analyzing a substance in the analysis apparatus 105.

The expected detection time period Ta103 can be set in advance, and therefore the expected detection time period Ta103 can be treated as a fixed time period having about several seconds. That is, the expected testing time period Ta103 can be set to a predetermined period in advance.

Similarly, an testing waiting time period in the security gate 300b is defined as Tb102, and an expected detection time period is defined as Tb103.

The expected detection time periods Ta103 and Tb103 and the prohibited time periods Ta111 and Tb111 are stored/set in a storage apparatus 291 in advance.

When, for example, the security gate 300a detects acquisition of information, it is desirable that the security gate system 2A according to Embodiment 2 prohibit operation of the units 221b to 223b of the security gate 300b until testing in the security gate 300a is terminated.

However, the security gate system 2A according to Embodiment 3 only needs to prohibit operation of the units 221b to 223b of the security gate 300b only in the set prohibited time period Tb111. Thus, the security gate system 2A according to Embodiment 3 can reduce the prohibited time period, and therefore it is possible to achieve efficient operation of the security gate system 2A.

The prohibited time periods Ta111 and Tb111 depend on lengths of the expected detection time periods. That is, it is only necessary to prevent the expected detection time period Ta103 in the security gate 300a from being overlapped with the expected detection time period Tb103 in the security gate 300b.

FIG. 9 shows examples of a prohibited time period obtained in the case where an expected detection time period is longer than an authentication/injection time period.

Figure 9A:
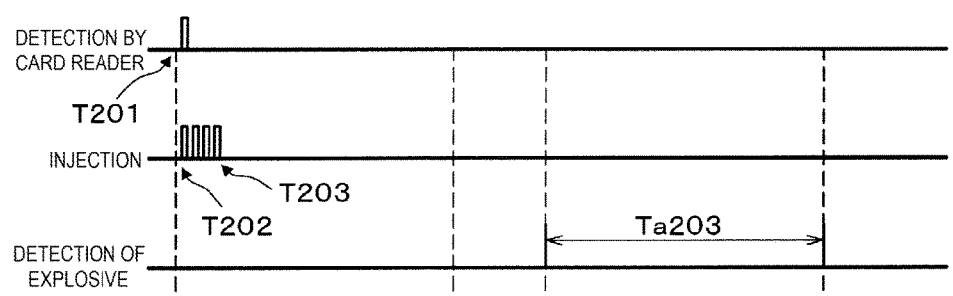
FIGS. 9A and 9B show examples of a prohibited time period obtained in the case where an expected detection time period is longer than an authentication/injection time period.

Herein, FIG. 9(a) shows time charts of detection of acquisition of information using the card reader 302a, injection of compressed air from the injection nozzle 311a, and detection of an explosive derived from the security gate 300a in order from the top.

In FIG. 9(a), a time T201 is a time at which the card reader 302a detects acquisition of information. A time T202 is a time at which injection of compressed air using the injection nozzle 311a is started, and a time T203 is a time at which the injection of the compressed air is terminated. Ta203 is an expected detection time period. In FIG. 9(a), a time at which the explosive derived from the security gate 300a is detected is not shown.

Figure 9B:
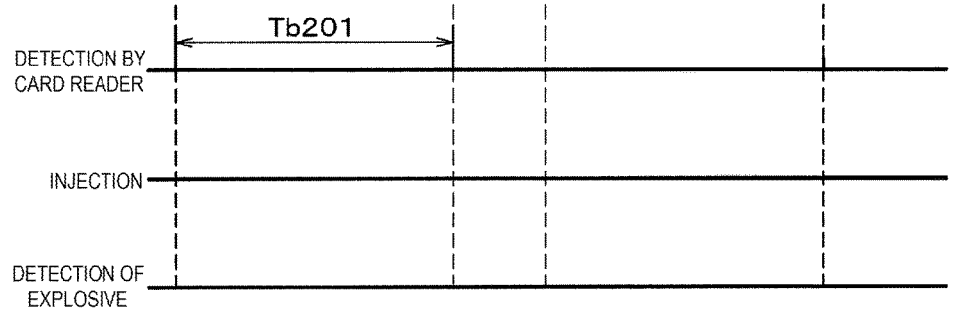

FIG. 9(b) shows time charts of detection of acquisition of information using the card reader 302b, injection of compressed air from the injection nozzle 311b, and detection of an explosive derived from the security gate 300b in order from the top.

Herein, Tb201 is a prohibited time period in the security gate 300b, which is caused when the security gate 300a acquires information from the IC card 30.

As shown in FIG. 9(a), in the case where the expected detection time period Ta203 is long, the prohibited time period Tb201 in the security gate 300b also becomes long in order to prevent the expected detection time period in the security gate 300b from being overlapped with the expected detection time period Ta203.

As described above, in this embodiment, the prohibited time periods Ta111 and Tb111 (FIG. 8) are set so that the expected detection time periods Ta103 and Tb103 (FIG. 8) in the security gate 300a and the security gate 300b are not overlapped with each other. Because the prohibited time periods Ta111 and Tb111 are set as described above, the analysis apparatus 105 does not analyze particles 10a acquired in the security gate 300a and particles 10b acquired in the security gate 300b at the same time. Thus, in the case where an explosive is detected in the expected detection time period Ta103 or Tb103 (FIG. 8), the analysis control unit 215 can determine whether this explosive is derived from the security gate 300a or the security gate 300b.

The security gate system 2A according to this embodiment is different from the security gate system in Embodiment 2 in that, even in the case where testing of the particles 10 derived from the security gate 300 that detected acquisition of information has not been terminated, the security gate system in this embodiment can cancel prohibition of operation of the security gate 300 that has not detected acquisition of information when the prohibited time period is terminated. Therefore, it is possible to reduce an operation prohibited time period in the security gate 300 that has not detected acquisition of information, and testing efficiency can be improved accordingly.

In the security gate system 2A according to this embodiment, an existing authenticate system and the particle testing system 1A can be provided together.

[Embodiment 4]

Embodiment 4 of the invention will be described with reference to FIG. 10 to FIG. 15. In Embodiment 4, a security gate system that can inspect particles 10 adhering to a luggage will be described.

(System Configuration)

FIG. 10 illustrates a detailed configuration example of a security gate system according to Embodiment 4.

Note that, in a security gate system (substance testing system) 2B in FIG. 10, configurations similar to the configurations in FIG. 1 and FIG. 4 are denoted by the same reference signs, and description thereof is omitted. That is, in FIG. 10, a particle testing apparatus 100 of a particle testing system 1B is similar to the particle testing apparatus 100 illustrated in FIG. 1, and a security gate 300a has a configuration similar to the configuration of the security gate 300a in FIG. 4. Therefore, description thereof is omitted, and configurations of a baggage testing unit 400 and a control apparatus 200B will be described.

The baggage testing unit 400 includes a belt conveyor 401, a particle peeling-off unit 301c (301), and a line sensor 402.

The belt conveyor 401 conveys baggage 411 and is driven by a driving unit 403.

An injection nozzle 311c (311) of the particle peeling-off unit 301c (301) injects pulsed compressed air by using an electromagnetic valve 321c (321) for a certain time period.

The line sensor 402 detects the baggage 411 on the belt conveyor 401.

A collection port 101c (101) collects particles 10c peeled off from the baggage 411 and introduces the collected particles into the introduction pipe 106b.

The control apparatus 200B will be described later.

FIG. 11 shows a configuration example of the control apparatus according to Embodiment 4. Note that, in FIG. 11, elements similar to elements in FIG. 1 are denoted by the same reference signs, and description thereof is omitted.

The control apparatus 200B includes not only the configurations of the control apparatus 200 described in Embodiment 1 but also a card reader control unit 221 (221a), injection nozzle control units 222 (222a and 222c), a gate flap control unit 223 (223a), a belt conveyor control unit 231, and a line sensor detection control unit 232.

The card reader control unit 221a, the injection nozzle control unit 222a, and the gate flap control unit 223a are similar to the card reader control unit 221a, the injection nozzle control unit 222a, and the gate flap control unit 223a in Embodiment 2, and therefore description thereof is omitted herein.

The belt conveyor control unit 231 controls the driving unit 403 of the belt conveyor 401, thereby controlling operation of the belt conveyor 401.

The injection nozzle control unit 222c controls the electromagnetic valve 321c (321) of the injection nozzle 311c (311) in the baggage testing unit 400 to control an injection frequency and the number of injection times of pulsed compressed air injected from the injection nozzle 311c.

The line sensor detection control unit 232 processes a signal transmitted from the line sensor 402.

A control unit 211B and the units 212 to 215, 221 to 223, 231, and 232 are realized in such a way that programs stored in a storage apparatus 291 are loaded into a memory 210 and are executed by a CPU 292.

(Outline of Processing)

An outline of operation of the baggage testing unit 400 in the security gate system according to Embodiment 4 will be described with reference to FIG. 10. Detailed operation of the security gate system 2B will be described later.

First, when the baggage 411 is placed on the belt conveyor 401 moving in a direction of an arrow 441 in FIG. 10, the baggage 411 is moved to a position of the line sensor 402.

When the baggage 411 passes through the line sensor 402, the control apparatus 200B measures a size of the baggage 411 by using the line sensor 402. In the case where a moving speed of the belt conveyor 401 is already known, the control apparatus 200B can obtain the size of the baggage 411 on the basis of a time at which the baggage passes through the line sensor 402.

Thereafter, the baggage 411 is moved to a position at which pulsed compressed air generated by the injection nozzle 311c is injected.

Based on the above information, the injection nozzle control unit 222c operates the electromagnetic valve 321c at a timing needed to efficiently peel off the particles 10c from the baggage 411 and causes the injection nozzle 311c to inject pulsed compressed air. In the case where the moving speed of the belt conveyor 401 is already known, the control unit 211B can calculate a time period required for moving the baggage 411 to the position at which pulsed compressed air is injected. Based on the time period required for moving, the control unit 211B obtains a time at which the baggage 411 passes through an area in which pulsed compressed air is injected, and, based on this time, the control unit 211B determines an injection timing of the compressed air. In this way, the particles 10c adhering to the baggage 411 are peeled off.

The particles 10c peeled off from the baggage 411 are transferred by an airflow caused by the compressed air injected from the injection nozzle 311c in a direction of the collection port 101c and are collected into the collection port 101c. That is, the collection port 101c is placed in the vicinity of the injection nozzle 311c.

Note that, in FIG. 10, a single line sensor 402 and a single injection nozzle 311c are installed for the sake of description. However, the baggage 411 has various sizes, and therefore it is desirable to provide a plurality of line sensors 402 and a plurality of injection nozzles 311c in combination as illustrated in, for example, FIG. 12 and FIG. 13.

(Line Sensor)

FIG. 12 illustrates a configuration example of arrangement of line sensors.

In the example illustrated in FIG. 12, the line sensor 402 include a plurality of light emission portions 421a to 421d and a plurality of light reception portions 422a to 422d. The light emission portions 421a to 421d emit, for example, infrared radiation lasers 423. The light emission portions 421a to 421d and the light reception portions 422a to 422d are placed in a vertical direction with respect to the baggage 411. With this configuration, the control unit 211B (FIG. 11) can detect the size (height) of the baggage 411 on the basis of whether or not the light reception portions 422a to 422d detect the infrared radiation lasers 423 emitted from the light emission portions 421a to 421d in the line sensor 402.

(Injection Nozzle)

FIG. 13 illustrates a configuration example of arrangement of injection nozzles.

In the example illustrated in FIG. 13, the injection nozzle 311c includes a plurality of injection nozzles 311c-1 to 311c-4. The injection nozzles 311c-1 to 311c-4 are placed in the vertical direction with respect to the baggage 411. In addition, the collection port 101c is installed to face to the injection nozzles 311c-1 to 311c-4.

The injection nozzle control unit 222c (FIG. 11) injects compressed air from any one or more of the injection nozzles 311c-1 to 311c-4 on the basis of information on the height of the baggage 411 detected by the line sensor 402. In this way, the particles 10c adhering to the baggage 411 are collected into the collection port 101c.

(Flowchart)

FIG. 14 is a flowchart showing a processing procedure in the security gate system according to Embodiment 4. FIG. 10, FIG. 11, and FIG. 13 will be referred to as appropriate.

In this embodiment, the security gate 300a and the baggage testing unit 400 are exclusively operated. With this, the control apparatus 200B can specify which one of the security gate 300a and the baggage testing unit 400 has detected an explosive.

Hereinafter, a method thereof will be described with reference to the flowchart, and processing in the security gate 300a is similar to the processing in FIG. 6 except that, in the processing in Step S114 of FIG. 6, the control unit 211B receives a notification of detection of baggage from the baggage testing unit 400. Therefore, description of the processing in the security gate 300a is omitted, and processing in the baggage testing unit 400 will be mainly described.

First, the injection nozzle control unit 222c of the control apparatus 200B causes the injection nozzle 311c to be in a standby state (S201). At this time, the belt conveyor 401 is already moving, but an infrared radiation sensor (not illustrated) maybe included in the belt conveyor 401 so that the belt conveyor 401 moves when a person approaches.

Then, the line sensor detection control unit 232 determines whether or not the baggage 411 has been detected by the line sensor 402 (S202). The line sensor detection control unit 232 performs determination in Step S202 by determining whether or not non-detection of the infrared radiation lasers 423 (FIG. 12) in the light reception portions 422a to 422d (FIG. 12) in the line sensor 402 has been detected.

As a result of Step S202, in the case where the baggage 411 has not been detected (S202→No), the control unit 211B advances the processing to Step S211.

As a result of Step S202, in the case where the baggage 411 is detected (S202→Yes), the line sensor detection control unit 232 notifies the control unit 211B that the baggage 411 has been detected (S203). The control unit 211B that has been notified of detection of the baggage 411 notifies the card reader control unit 221a, the injection nozzle control unit 222a, and the gate flap control unit 223a of the security gate 300a that the baggage 411 has been detected.

Note that detection of the baggage 411 in Step S202 also means that the control apparatus 200B has detected collection of the particles 10c in the collection port 101c.

After the baggage 411 is detected in Step S202, the belt conveyor control unit 231 and the injection nozzle control unit 222c may prohibit operation of the belt conveyor 401 and the injection nozzle 311c until analysis of the collected particles 10c is completed.

Then, when the baggage 411 is moved to a position of the injection nozzle 311c by the belt conveyor 401, the injection nozzle control unit 222c injects pulsed compressed air from the injection nozzle 311c (S204). By injecting the compressed air from the injection nozzle 311c, the particles 10c are peeled off from the baggage 411.

Note that, as described above, an injection timing of the injection nozzle 311c is calculated by the control unit 211B on the basis of the moving speed of the belt conveyor 401, a detection time of the baggage 411, and the like.

The particles 10c peeled off from the baggage 411 are collected by the collection port 101c and are transferred to the centrifuge 102b.

The centrifuge 102b centrifuges the transferred particles 10c, thereby separating the particles 10c from air to concentrate the particles 10c (S205).

The separated and concentrated particles 10c are heated by the heating filter 103 in the heating block 104 (S206) to be vaporized.

Then, the analysis apparatus 105 analyzes the vaporized particles 10c (S207).

The analysis apparatus 105 transmits an analysis result to the control apparatus 200B, and the analysis control unit 215 determines whether or not an explosive has been detected (S208).

As a result of Step S208, in the case where an explosive has been detected (S208→Yes), the control unit 211B performs detection processing (S209) and returns the processing to Step S201. In the detection processing, for example, the control unit 211B causes the gate flap control unit 223a of the control apparatus 200B to close the gate flap 303a and causes a security system (not illustrated) to issue a warning. The belt conveyor control unit 231 forcibly stops the belt conveyor 401. At this time, the control unit 211B associates information of the IC card 30 read by the card reader 302a with a result of detection of the explosive and causes the security system (not illustrated) to issue a warning. That is, the control unit 211B associates the analysis result in the analysis apparatus 105 with the information read from the IC card 30. The information of the IC card 30 at this time may be read within a predetermined time period after detection of the baggage 411.

When the control unit 211B returns the processing to Step S201 after the detection processing in Step S209 is terminated, the security gate system 2B continues normal processing even in the case where the explosive has been detected. With this, it is possible to catch the target person 20 (FIG. 2) who possesses the explosive or the baggage 411 at a safe place while such detection of the explosive is not being noticed by the target person 20.

Note that, in the case where it is desirable to catch the baggage 411 containing the explosive immediately, the control unit 211B may terminate the processing after Step S209.

As a result of Step S208, in the case where no explosive has been detected (S208→No), the control unit 211B notifies the card reader control unit 221a, the injection nozzle control units 222a, and the gate flap control unit 223a of the security gate 300a that testing in the baggage testing unit 400 has been terminated (S210).

Then, the control unit 211B determines whether or not notification of acquisition of information of the IC card 30 (FIG. 3) has been received from the card reader control unit 221a of the security gate 300a (S211). This notification has been transmitted in Step S105 of FIG. 6 in the security gate 300a.

As a result of Step S211, in the case where the notification of the acquisition of the information of the IC card 30 has not been received from the security gate 300a (S211→No), the control unit 211B returns the processing to Step S201.

As a result of Step S211, in the case where the notification of the acquisition of the information of the IC card 30 is received from the security gate 300a (S211→Yes), the injection nozzle control unit 222c prohibits injection using the injection nozzle 311c (S212).

Then, the belt conveyor control unit 231 forcibly stops the belt conveyor 401 (S213).

By the processing in Steps S212 and S213, the collection port 101c is prohibited from collecting the particles 10c.

Then, the control unit 211B determines whether or not notification of termination of the testing has been received from the security gate 300a (S214). This notification has been transmitted in Step S112 of FIG. 6 in the security gate 300b.

As a result of Step S214, in the case where the notification of the termination of the testing has not been received from the security gate 300a (S214→No), the control unit 211B returns the processing to Step S211.

As a result of Step S214, in the case where the notification of the termination of the testing is received from the security gate 300a (S214→Yes), the control unit 211B returns the processing to Step S201. That is, the control unit 211B cancels prohibition of injection using the injection nozzle 311a and a state in which the belt conveyor 401 is forcibly stopped.

According to this embodiment, it is possible to not only obtain effects similar to the effects of the particle testing system 1 and the security gate system 2A according to Embodiments 1 to 3 but also perform testing of the particles 10a adhering to the IC card 30 (FIG. 3) and testing of the particles 10c adhering to the baggage 411 with the use of the same analysis apparatus 105.

That is, according to security gate system 2B in this embodiment, it is possible to perform entry/exit management in public facilities such as airports, harbors, ticket gates in stations, commercial facilities, office buildings, and amusement facilities and testing of the baggage 411 possessed by the target person 20 (FIG. 2) at the same time. It is also possible to perform entry/exit management and, for example, testing of a delivered parcel in parallel.

Note that, as in Embodiment 2, in the processing shown in FIG. 14, the operation of the injection nozzle 311c and the belt conveyor 401 is prohibited until testing in the security gate 300a is terminated. On the contrary, as shown in FIG. 15, when a predetermined prohibited time period is terminated after operation of the injection nozzle 311c and the belt conveyor 401 is prohibited, prohibition of the operation of the injection nozzle 311c and the belt conveyor 401 may be canceled even in the case where testing in the security gate 300a has not been terminated.

That is, as shown in FIG. 15, after Step S212, the control unit 211B determines whether or not a prohibited time period in the baggage testing unit 400 of the security gate 300a has been terminated (S214A). The prohibited time period is a time period in which operation of the injection nozzle 311c and the belt conveyor 401 is prohibited after notification of acquisition of information is received from the security gate 300a. The prohibited time period is set to a certain time period in advance by a method similar to the method shown in FIG. 8 and FIG. 9. That is, the prohibited time period is set so that an expected detection time period in the security gate 300a is not overlapped with an expected detection time period in the baggage testing unit 400.

As a result of Step S214A, in the case where the prohibited time period has not been terminated (S214A→No), the control unit 211B returns the processing to Step S211.

As a result of Step S214A, in the case where the prohibited time period is terminated (S214A→Yes), the control unit 211B returns the processing to Step S201.

The other processing in FIG. 15 is similar to the processing in FIG. 14. The processing in the security gate 300a is similar to the processing in FIG. 7 except that, in the processing in Step S114 of FIG. 7, the control unit 211B receives a notification of detection of baggage from the baggage testing unit 400.

According to the processing shown in FIG. 15, as in Embodiment 3, it is possible to reduce an operation prohibited time period in the security gate 300 that has not detected acquisition of information, and testing efficiency can be improved accordingly.

Note that a tag reader (not illustrated) may be installed in the vicinity of the belt conveyor 401 so that information is read from an IC tag or the like attached to the baggage 411.

[Embodiment 5]

Embodiment 5 of the invention will be described with reference to FIG. 16 to FIG. 21.

(System Configuration)

FIG. 16 illustrates an external appearance example of a security station according to Embodiment 5.

A security station (substance testing system) 3 in Embodiment 5 includes four security checkers 500.

Herein, each of the security checkers 500 includes a particle peeling-off unit 301 (301d to 301g), a card reader 302 (302d and 302e), an image pickup apparatus (image acquisition unit) 501 (501d and 501e), and a collection port 101 (101d to 101g).

Note that FIG. 16 shows only the particle peeling-off units 301d and 301e, the card readers 302d and 302e, the image pickup apparatuses 501d and 501e, and the collection ports 101d and 101e. However, the particle peeling-off units 301f and 301g, card readers 302f and 302g, and image pickup apparatuses 501f and 501g shown in FIG. 17 are hidden on an opposite side of the side shown in FIG. 16.

The image pickup apparatuses 501 (501d and 501e) capture an image of a person serving as a target to be inspected. The image pickup apparatuses 501 are digital cameras, digital video cameras, or the like. As shown in FIG. 16, each of the image pickup apparatuses 501 is provided at a position at which an image of a person who has used the card reader 302 can be captured. The image pickup apparatus 501 may be provided at any place as long as the place is a position at which an image of a person who has used the card reader 302 can be captured.

FIG. 17 illustrates a detailed configuration example of the security station according to Embodiment 5.

As described above, the security station 3 in this embodiment includes the four security checkers 500. Note that the number of the security checkers 500 is not limited to four.

A configuration of each of the individual security checkers 500 (500d to 500g) is similar to the configuration of the security gate 300 illustrated in FIG. 4 except that the image pickup apparatuses 501 (501d to 501g) are provided and the gate flaps 303 (FIG. 4) are not provided, and therefore description thereof is omitted herein.

As described above, the image pickup apparatuses 501 (501d to 501g) capture an image of a person serving as a target to be inspected.

Although each unit of the security station 3 is controlled by a control apparatus 200C (FIG. 19), details of the control apparatus 200C will be described later and are not shown herein.

The other configurations 101 to 111 of a particle testing apparatus 100C are four groups of the configurations 101 to 111 illustrated in FIG. 1, and therefore description thereof is omitted.

Note that, although branched parts of a branch pipe 108D extending from the centrifuges 102 connected to the individual security checkers 500 have different distances from the individual centrifuges 102 in FIG. 17 because FIG. 17 is a schematic diagram, the individual centrifuges 102 are actually placed on a concentric circle around a branch point 601, and therefore distances between the centrifuges 102 and the branch point are equal.

As illustrated in FIG. 18, a plurality of branch points 611 to 613 may be provided in a single branch pipe 108E. As described above, when the branch pipe 108E having the plurality of branch points 611 to 613 is used, distances between the centrifuges 102d to 102g and the heating filter 103 can be equalized even in the case where a large number of centrifuges 102 are provided. With this, it is possible to minimize variation of a condition such as a time period in which the particles 10 separated in the centrifuge 102 reach the heating filter 103 or the analysis apparatus 105.

FIG. 19 illustrates a configuration example of a control apparatus according to Embodiment 5.

The control apparatus 200C includes a card reader control unit 221, an injection nozzle control unit 222, a fan control unit 212, a temperature adjustment unit 213, a pipe heater control unit 214, an analysis control unit 215, and an image pickup control unit 241.

The card reader control unit 221 is similar to the card reader control unit 221 in Embodiments 2 to 4 except that the card reader control unit 221 controls the four card readers 302d to 302g.

The injection nozzle control unit 222 is similar to the card reader control unit 221 in Embodiments 2 to 4 except that the injection nozzle control unit 222 controls electromagnetic valves 321d to 321g of four injection nozzles 311d to 311g.

The fan control unit 212 is similar to the fan control unit 212 in Embodiments 1 to 4 except that the fan control unit 212 controls four fans 107d to 107g.

The temperature adjustment unit 213, the pipe heater control unit 214, and the analysis control unit 215 are similar to the temperature adjustment unit 213, the pipe heater control unit 214 and the analysis control unit 215 in Embodiments 1 to 4.

The image pickup control unit 241 controls the image pickup apparatuses 501d to 501g (501) and acquires images captured by the image pickup apparatuses 501d to 501g (501).

(Flowchart)

FIG. 20 is a flowchart showing an operation procedure of the security station according to Embodiment 5.

In the flowchart shown in FIG. 20, processing different from the processing in Embodiment 2 (FIG. 6) is as follows.

First, the processing in Steps S102, S113, and S117 regarding the gate flap in FIG. 6 is omitted.

Then, in Step S105, acquisition of information in the card readers 302 is detected, and thereafter the image pickup control unit 241 causes the image pickup apparatuses 501 of the security checkers 500 that have detected the acquisition of the information to capture images of target persons 20a and 20b (S301).

Further, in the case where an explosive has been detected in Step S110 (S110→Yes), a control unit 211C performs detection processing (S302) and returns the processing to Step S101. In this detection processing, the control unit 211C performs processing in which, for example, the images captured in Step S301 are transmitted to a security system (not illustrated). Alternatively, the control unit 211C links detection of the explosive, the captured images, and information of the IC cards 30 (FIG. 3) read by the card readers 302 with one another and stores the linked information in a storage apparatus 291. That is, the control unit 211C associates the images captured by the image pickup apparatuses 501 with analysis results in the analysis apparatus 105. Note that this association may be performed, regardless of detection/non-detection of the explosive. Furthermore, the control unit 211C associates the images captured by the image pickup apparatuses 501, the analysis results in the analysis apparatus 105, and the information of the IC cards 30 read by the card readers 302 with one another.

With this, a target person 20 who possesses the explosive can be easily specified.

In addition, in Step S114, the control unit 211C determines whether or not information of the IC card 30 (FIG. 3) has been acquired from other security checker 500 than the security checker 500 serving as a target to be processed.

Further, when the control unit 211C returns the processing to Step S101 after the detection processing in Step S302 is terminated, the security station 3 continues normal processing even in the case where the explosive has been detected. With this, it is possible to catch the target person 20 (FIG. 2) who possesses the explosive at a safe place while such detection of the explosive is not being noticed by the person.

Note that, in the case where it is desirable to catch the target person 20 who possesses the explosive immediately, the control unit 211C may terminate the processing after Step S302.

In the security station 3 according to Embodiment 5, detection of an explosive adhering to the IC card 30 (FIG. 3) or the like can be performed by the plurality of security checkers 500.

The security station 3 according to Embodiment 5 includes the image pickup apparatuses 501, and therefore it is possible to link detection of the explosive with a captured image (person) or the like. With this, a person who possesses the explosive can be easily specified.

As shown in FIG. 21, Step S118 in FIG. 20 can be replaced with Step S118C which is processing in which the control unit 211C determines whether or not a prohibited time period of the security checker 500 serving as a target to be processed has been terminated. With this, as in Embodiment 3, the security station 3 can start next particle testing without waiting termination of the whole testing processing in the security checker 500 that has detected acquisition of information of the IC card 30 (FIG. 3).

[Embodiment 6]

FIG. 22 illustrates a configuration example of a security gate system according to Embodiment 6.

In Embodiments 1 to 5, the distances between the centrifuges 102 and the heating filter 103 are equal in the branch pipes 108 (FIG. 6), 108D (FIG. 17), and 108E (FIG. 18).

However, as in a particle testing apparatus 100D of a security gate system 2C in FIG. 22, distances between a branch point 621 and centrifuges 102 (102a and 102d) may be different in a branch pipe 108F. That is, distances between the centrifuges 102 (102a and 102d) and a heating filter 103 may be different.

Note that, in FIG. 22, configurations other than a configuration of the branch pipe 108F are similar to the configurations illustrated in FIG. 4. Although the control apparatus 200 (FIG. 4) is not shown, a configuration of the control apparatus 200 is similar to the configuration shown in FIG. 5. In FIG. 22, the configurations of the security gates 300a and 300b are not shown.

The above security gate system 2C can perform the processing described in Embodiment 2 and Embodiment 3.

Note that, in the method of setting a predetermined prohibited time period as in Embodiment 3, for example, the prohibited time period is set as shown in FIG. 23.

FIG. 23 shows examples of a prohibited time period in the security gate system according to Embodiment 6.

FIG. 23 shows examples where a length of a branched part of the branch pipe 108F connected to the centrifuge 102a is short and a length of a branched part of the branch pipe 108F connected to the centrifuge 102b is long as illustrated in FIG. 22.

Figure 23A:
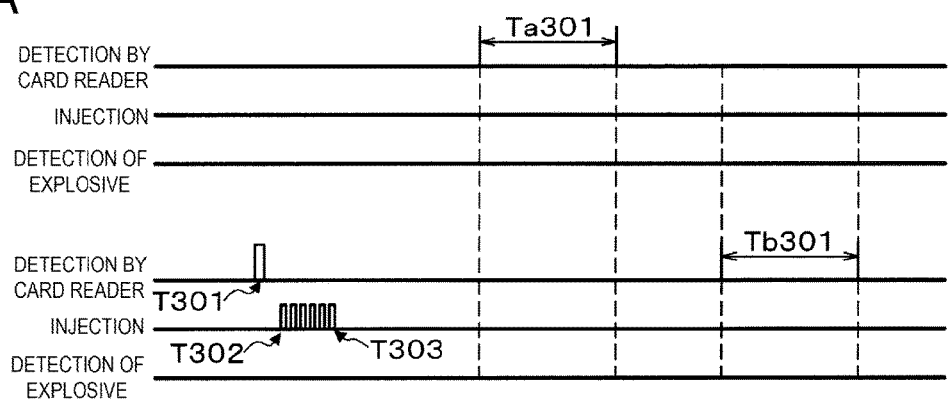
FIGS. 23A and 23B show examples of a prohibited time period in the security gate system according to Embodiment 6.

Herein, FIG. 23(a) shows, in order from the top, detection of acquisition of information using the card reader 302a, injection of compressed air from the injection nozzle 311a, detection of an explosive derived from the security gate 300a, detection of acquisition of information using the card reader 302b, injection of compressed air from the injection nozzle 311b, and detection of an explosive derived from the security gate 300b.

In FIG. 23(a), a time T301 is a time at which the card reader 302b detects acquisition of information. A time T302 is a time at which injection of compressed air using the injection nozzle 311b is started, and a time T303 is a time at which injection of the compressed air is terminated. Tb301 is an expected detection time period. Note that, in FIG. 23(a), a time at which an explosive is detected is not shown.

In such a case, a prohibited time period in the security gate 300a is a period Ta301.

Figure 23B:
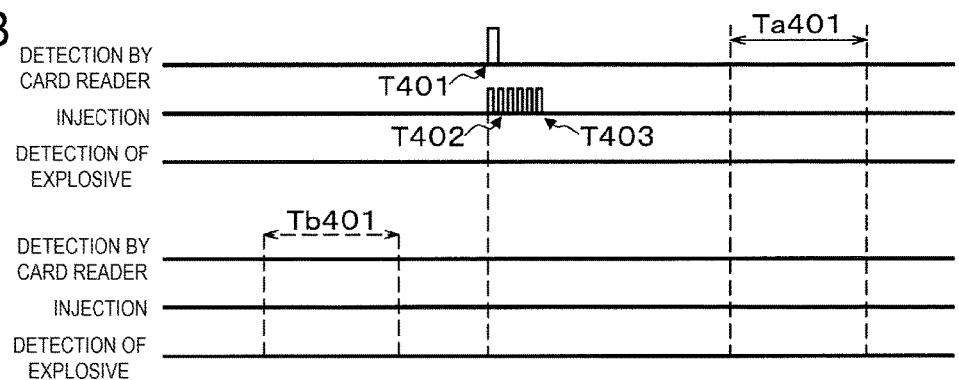

FIG. 23(b) also shows, in order from the top, detection of acquisition of information using the card reader 302a, injection of compressed air from the injection nozzle 311a, detection of an explosive derived from the security gate 300a, detection of acquisition of information using the card reader 302b, injection of compressed air from the injection nozzle 311b, and detection of an explosive derived from the security gate 300b.

In FIG. 23(b), a time T401 is a time at which the card reader 302a detects acquisition of information. A time T402 is a time at which injection of compressed air using the injection nozzle 311a is started, and a time T403 is a time at which injection of the compressed air is terminated. Ta401 is an expected detection time period. Note that, in FIG. 23(b), a time at which an explosive is detected is not shown.

In such a case, a prohibited time period in the security gate 300b is a period Tb401.

Herein, the prohibited time period Tb401 is a time before the time T401 at which acquisition of information of the security gate 300a is detected.

That is, in the example of FIG. 23, it is unnecessary to set a prohibited time period in the security gate 300b.

As described above, a setting time of the prohibited time period depends on the length of the branch pipe 108F. That is, in the case where the length of the branch pipe 108F is short, the setting time of the prohibited time period is set to be a late time. On the contrary, in the case where the length of the branch pipe 108F is long, the setting time of the prohibited time period is set to be an early time.

As described above, according to the security gate system in this embodiment, it is possible to set a prohibited time period even in the case where the lengths between the centrifuges 102 and the heating filter 103 (or the analysis apparatus 105) are different.

As shown in FIG. 23, in the case where the other part of the branch pipe 108F is extremely longer than one part of the branch pipe 108F, in some cases, it is unnecessary to set the prohibited time period in the security gate 300 connected to the branch pipe 108F.

[Embodiment 7]

Embodiment 7 of the invention will be described with reference to FIG. 24.

(System Configuration)

FIG. 24 illustrates a configuration example of a particle testing system according to Embodiment 7. Note that, in FIG. 24, elements similar to the elements in FIG. 1 are denoted by the same reference signs, and therefore description thereof is omitted.

A particle testing system 1D illustrated in FIG. 24 is different from the particle testing system 1 illustrated in FIG. 1 in that, in a particle testing apparatus 100D, a branch point 701 of a branch pipe 108 is positioned outside a heating block 104. More specifically, the branch point 701 of the branch pipe 108 is positioned on an upstream side of the heating block 104.

With this, as in Embodiment 1, the particle testing apparatus 100D can be used as a mass spectrometer. In addition, because a heating filter 103 is provided on a downstream side of a merged part (branch point 701) in the branch pipe 108, it is only necessary to provide the single heating filter 103. With this, cost reduction can be achieved.

[Embodiment 8]

Embodiment 8 of the invention will be described with reference to FIG. 25.

(System Configuration)

FIG. 25 illustrates a configuration example of a particle testing system according to Embodiment 8. Note that, in FIG. 25, elements similar to the elements in FIG. 1 are denoted by the same reference signs, and therefore description thereof is omitted.

A particle testing system 1E illustrated in FIG. 25 is different from the particle testing system 1 illustrated in FIG. 1 in that, in a particle testing apparatus 100E, a branch point 702 of a branch pipe 108 is positioned outside heating blocks 104a and 104b. More specifically, the branch point 702 of the branch pipe 108 is positioned on a downstream side of the heating blocks 104a and 104b.

The particle testing apparatus 100E includes the heating block 104a corresponding to a centrifuge 102a and the heating block 104b corresponding to a centrifuge 102b. That is, the particle testing apparatus 100E includes the heating blocks 104a and 104b corresponding to the plurality of centrifuges 102a and 102b. In other words, in the particle testing apparatus 100E, the heating blocks 104a and 104b and the corresponding collection ports 101a and 101b are installed in pairs.

The heating block 104a includes a heating filter 103a, a heating heater 109a, and a temperature sensor 110a (110). Similarly, the heating block 104b includes a heating filter 103b, a heating heater 109b, and a temperature sensor 110b. The heating filters 103a and 103b, the heating heaters 109a and 109b, and the temperature sensors 110a and 110b are similar to the heating filter 103, the heating heaters 109, and the temperature sensor 110 in FIG. 1, respectively, and therefore description thereof is omitted herein.

As illustrated in FIG. 25, a pipe heater 112 in the particle testing apparatus 100E covers outer circumferences of the branch pipe 108 and a pipe 111 from outlet ports of the heating blocks 104a and 104b to the analysis apparatus 105 via the branch point 702.

As illustrated in FIG. 25, the heating filters 103a and 103b heat and evaporate (vaporize) the particles 10a and 10b sent from the centrifuges 102a and 102b respectively connected thereto. The heating filter 103a and the particles 10a are, for example, brought into contact with each other, and therefore a vapor component is generated from the particles 10a. This vapor component is introduced into the analysis apparatus 105 through the branch pipe 108 and the pipe 111 because of an influence of suction of the analysis apparatus 105.

Similarly, the heating filter 103b and the particles 10b are, for example, brought into contact with each other, and therefore a vapor component is generated from the particles 10b. This vapor component is introduced into the analysis apparatus 105 through the branch pipe 108 and the pipe 111 because of an influence of suction of the analysis apparatus 105.

The control apparatus 200E is different from the control apparatus 200 in FIG. 1 in that the control apparatus 200E includes temperature adjustment units 213a and 213b for controlling the two heating blocks 104a and 104b, respectively.

The particle testing system 1E in Embodiment 8 have two effects described below.

(1) Temperatures of the individual heating blocks 104a and 104b can be set to different temperatures. With this, more explosive substance particles can be vaporized at optimal heating temperatures. Specifically, the particles 10 having a comparatively high volatility, such as TNT, are efficiently heated and evaporated (vaporized) at about 200° C. However, when the temperature is too high, thermal decomposition is excessively advanced, and therefore detection efficiency is reduced. On the contrary, the particles 10 having a comparatively low volatility, such as a military explosive, are efficiently heated and evaporated (vaporized) at about 250° C. However, when the temperature is low, it takes time to vaporize the particles, thereby affecting an testing throughput.

As described above, there is a temperature suitable for detecting the particles 10. According to this embodiment, when temperatures of the individual heating blocks 104a and 104b are set to different temperatures, it is possible to separately heat the particles 10a and 10b at temperatures suitable for the particles 10a and 10b.

(2) Even in the case where breakage of one of the heating blocks 104a and 104b occurs and the particles 10 cannot be detected, the other one of the heating blocks 104a and 104b can be used, and therefore detection of the particles 10 can be continued. That is, robustness of the particle testing system 1E can be improved. The breakage in this case means, for example, a malfunction caused by disconnection or the like of the heating heaters 109a and 109b and the temperature sensors 110a and 110b and a malfunction caused by clogging of the heating filters 103a and 103b.

Note that the invention is not limited to the above embodiments and includes various modification examples. For example, the above embodiments have been described in detail to easily understand the invention, and therefore the invention is not necessarily limited to the embodiments having all the configurations described above. Further, a part of a configuration of a certain embodiment can be replaced with a configuration of another embodiment, and a configuration of another embodiment can be added to a configuration of a certain embodiment. Further, another configuration can be added to, removed from, or replaced with a part of a configuration of each embodiment.

The security gate systems 2A and 2B in the embodiments inspect the particles 10 adhering to the IC card 30 (FIG. 3). However, the security gate systems may inspect the particles 10 adhering to not only the IC card 30 but also an IC tag, a pass including an IC microchip, a passport, or the like.

The security gate systems 2A and 2B and the security station 3 in the embodiments may be combined with a fingerprint authentication apparatus, a retinal scan, or an iris authentication apparatus.

Although the embodiments disclose the cases where the particles 10 from the IC card 30 or the baggage 411 are inspected, the embodiments are not limited thereto, and, for example, a security gate system may be formed such that a fingerprint authentication apparatus includes a particle peeling-off unit 301 and a collection port 101 so as to inspect the particles 10 adhering to a finger of a person.

Alternatively, a security gate system may be formed such that an apparatus for injecting compressed air toward the whole body of a person includes a collection port 101 so as to inspect particles adhering to clothes or the like of a person.

The security gate systems 2A and 2B and the security station 3 may inspect the particles 10 adhering to specific parts of a human body such as a foot and hair, shoes, bags, and the like.

The image pickup apparatus 501 in Embodiment 5 may be, for example, an infrared camera for acquiring an image based on a quantity of heat generated from a living body or an image pickup apparatus to which an image filter for reading specific information such as a badge on breast is applicable.

The configurations, the functions, the control apparatuses 200, 200A, 200B, and 200C, the storage apparatus 291, and the like described above may be realized with hardware by, for example, designing a part or all thereof with an integrated circuit. Alternatively, the configurations, the function, and the like described above may be realized with software by a processor such as the CPU 292 interpreting and executing programs for realizing the respective functions. Information such as the programs for realizing the functions, tables, and files can be stored in the storage apparatus 291 such as an HD (Hard Disk) or can be stored in a recording apparatusesuch as a memory or an SSD (Solid State Drive) or a recording medium such as an IC card, an SD (Secure Digital) card, or a DVD (Digital Versatile Disc).

Further, in each embodiment, control lines and information lines, which are considered to be needed for the description, are shown, and not all control lines and information lines are necessarily shown in terms of a product. Actually, it may be considered that almost all of the configurations are connected to one another.

REFERENCE SIGNS LIST 1, 1A, 1B, 1D, 1E particle testing system (substance testing system)
2, 2A, 2B security gate system (substance testing system)
3 security station (substance testing system)
10, 10a to 10c particle (substance)
30 IC card (information recording medium)
100, 100C, 100D, 100E particle testing apparatus
101, 101a to 101g collection port (collection unit)
102, 102a, 102b, 102d to 102g centrifuge (concentration unit)
103 heating filter (heating unit)
104, 104a, 104b heating block
105 analysis apparatus (analysis unit)
106, 106a, 106b, 106d to 106g introduction pipe
107, 107a, 107b, 107d to 107g exhaust fan
108, 108D, 108E, 108F branch pipe
200, 200A, 200B, 200C control apparatus
211, 211A, 211B, 211C control unit
212, 212a, 212b fan control unit
213, 213a, 213b temperature adjustment unit
214 pipe heater control unit
215 analysis control unit
221, 221a, 221b card reader control unit
222, 222a, 222b, 222c injection nozzle control unit
223, 223a, 223b gate flap control unit
231 belt conveyor control unit
232 line sensor detection control unit
300, 300a, 300b security gate
301, 301a, 301b particle peeling-off unit (peeling-off unit)
302, 302a, 302b card reader
303, 303a, 303b gate flap
311, 311a to 311c injection nozzle (peeling-off unit)
321, 321a to 321c electromagnetic valve
400 baggage testing unit
401 belt conveyor
402 line sensor
500, 500d to 500g security checker
501, 501d to 501g image pickup apparatus (image acquisition unit)
Ta103, Tb103, Ta203, Tb301, Ta401 expected detection time period
Ta111, Tb111, Tb201, Ta301, Tb401 prohibited time period

The invention claimed is:
1. A substance testing system, comprising:
a substance testing apparatus including
a plurality of collection units for collecting substances to be inspected,
concentration units for concentrating the substances collected in the collection units, the concentration units being connected to the respective collection units in pairs, and
a common analysis unit for acquiring the concentrated substances from the concentration units and analyzing the substances, the analysis unit being connected to the concentration units;
a control apparatus for controlling permission and prohibition of collection of the substances, wherein
when a certain collection unit of the plurality of collection units collects the substance, the control apparatus prohibits the other collection units from collecting the substance, and wherein
the substance testing system further comprises a heating unit for heating the substances to vaporize the substances, the heating unit being provided on the analysis unit side from a point at which the substances sent from the concentration units are merged.

2. The substance testing system according to claim 1, wherein lengths between the concentration units and the analysis unit are the same.

3. The substance testing system according to claim 1, further comprising
a substance peeling-off unit for peeling off a substance from a target to be inspected, the substance peeling-off unit being provided in the vicinity of the collection unit.

4. The substance testing system according to claim 1, further comprising
an information reading unit for reading information of an information recording medium on which information is recorded, the information reading unit being provided in the vicinity of the collection unit, wherein
the control apparatus associates the information of the information recording medium read by the information reading unit with an analysis result in the analysis unit.

5. The substance testing system according to claim 1, further comprising
an image acquisition unit for acquiring an image, wherein
the control apparatus associates the image acquired by the image acquisition unit with an analysis result in the analysis unit.

6. The substance testing system according to claim 1, further comprising
a peeling-off unit for peeling off a substance adhering to baggage, the peeling-off unit being provided in the vicinity of the collection unit.

7. A substance testing system, comprising:
a substance testing apparatus including
a plurality of collection units for collecting substances to be inspected,
concentration units for concentrating the substances collected in the collection units, the concentration units being connected to the respective collection units in pairs, and
a common analysis unit for acquiring the concentrated substances from the concentration units and analyzing the substances, the analysis unit being connected to the concentration units;
a control apparatus for controlling permission and prohibition of collection of the substances, wherein
the control apparatus has, in a storage unit, information on an expected detection time period that is an expected time period required for analyzing a substance in the analysis unit; and
the control apparatus sets a prohibited time period that is a time period in which collection of the substance is prohibited so that the expected detection time periods in the respective concentration units are not overlapped, and
when a certain collection unit of the plurality of collection units collects the substance, the other collection units are prohibited from collecting the substance in the prohibited time period.

8. The substance testing system according to claim 7, wherein
lengths between the concentration units and the analysis unit are the same.

9. The substance testing system according to claim 7, further comprising
a substance peeling-off unit for peeling off a substance from a target to be inspected, the substance peeling-off unit being provided in the vicinity of the collection unit.

10. The substance testing system according to claim 7, further comprising
an information reading unit for reading information of an information recording medium on which information is recorded, the information reading unit being provided in the vicinity of the collection unit, wherein
the control apparatus associates the information of the information recording medium read by the information reading unit with an analysis result in the analysis unit.

11. The substance testing system according to claim 7, further comprising
an image acquisition unit for acquiring an image, wherein
the control apparatus associates the image acquired by the image acquisition unit with an analysis result in the analysis unit.

12. The substance testing system according to claim 7, further comprising
a peeling-off unit for peeling off a substance adhering to baggage, the peeling-off unit being provided in the vicinity of the collection unit.

13. A substance testing method, wherein
in a substance testing system including
a substance testing apparatus including
a plurality of collection units for collecting substances to be inspected,
concentration units for concentrating the substances collected in the collection units, the concentration units being connected to the respective collection units in pairs, and
a common analysis unit for acquiring the concentrated substances from the concentration units and analyzing the substances, the analysis unit being connected to the concentration units, and
a control apparatus for controlling permission and prohibition of collection of the substances, wherein
the control apparatus has, in a storage unit, information on an expected detection time period that is an expected time period required for analyzing a substance in the analysis unit, and the control apparatus sets a prohibited time period that is a time period in which collection of the substance is prohibited so that the expected detection time periods in the respective concentration units are not overlapped, and
when a certain collection unit of the plurality of collection units collects the substance, the control apparatus prohibits the other collection units from collecting the substance in the prohibited time period.

14. The substance testing method according to claim 13, further comprising
an information reading unit for reading information of an information recording medium on which information is recorded, the information reading unit being provided in the vicinity of the collection unit, wherein
the control apparatus associates the information of the information recording medium read by the information reading unit with an analysis result in the analysis unit.

* * * * *